US009427373B2

(12) United States Patent
Sankai

(10) Patent No.: US 9,427,373 B2
(45) Date of Patent: *Aug. 30, 2016

(54) WEARABLE ACTION-ASSIST DEVICE AND CONTROL PROGRAM

(71) Applicant: UNIVERSITY OF TSUKUBA, Tsukuba-Shi, Ibaraki (JP)

(72) Inventor: Yoshiyuki Sankai, Tsukuba (JP)

(73) Assignee: UNIVERSITY OF TSUKUBA, Tsukuba-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/561,933

(22) Filed: Dec. 5, 2014

(65) Prior Publication Data

US 2015/0150747 A1 Jun. 4, 2015

Related U.S. Application Data

(60) Division of application No. 12/881,796, filed on Sep. 14, 2010, now Pat. No. 8,932,241, which is a continuation of application No. 11/795,907, filed as application No. PCT/JP2005/021472 on Nov. 22, 2005, now Pat. No. 7,857,774.

(30) Foreign Application Priority Data

Jan. 26, 2005 (JP) ................. 2005-018295

(51) Int. Cl.
*A61H 3/00* (2006.01)
*B25J 9/00* (2006.01)
(Continued)

(52) U.S. Cl.
CPC .............. *A61H 3/00* (2013.01); *A61B 5/04001* (2013.01); *A61H 1/0255* (2013.01); *A61H 3/008* (2013.01);
(Continued)

(58) Field of Classification Search
CPC ...... A61H 3/00; A61H 3/008; A61H 1/0255; A61H 2201/5061; A61H 2201/1676; A61H 2201/1642
See application file for complete search history.

(56) References Cited

U.S. PATENT DOCUMENTS 3,631,542 A 1/1972 Potter
3,735,425 A * 5/1973 Hoshall ............... A61B 5/0428
623/25
(Continued)

FOREIGN PATENT DOCUMENTS

EP 1 410 780 A1 4/2004
EP 1 475 194 A1 11/2004
(Continued)

OTHER PUBLICATIONS

Patent Abstracts of Japan of JP 07-163607 dated Jun. 21, 1995.
(Continued)

*Primary Examiner* — Quang D Thanh
*Assistant Examiner* — Timothy Stanis
(74) *Attorney, Agent, or Firm* — Ladas & Parry LLP

(57) ABSTRACT

A wearable action-assist device includes a biosignal detection unit detecting a biosignal from a wearer, an action-assist wearing tool having a drive source supplying a torque acting on the wearer around each joint of the wearer as an axis of rotation, a control unit controlling the drive source to generate the torque according to the detected biosignal, a drive torque estimation unit estimating a drive torque generated by the drive source, a joint-angle detecting unit detecting an angular displacement of the joint, and a parameter identification unit identifying kinetics parameters concerned by substituting the estimated drive torque and the detected angular displacement into an equation of motion of an entire system including kinetics parameters intrinsic to the wearer. The control unit is configured to control the drive source according to a predetermined control method based on the equation of motion into which the identified parameters are substituted.

3 Claims, 21 Drawing Sheets

(51) Int. Cl.
*A61H 1/02* (2006.01)
*A61B 5/04* (2006.01)
*A63B 23/04* (2006.01)
*A63B 24/00* (2006.01)

(52) U.S. Cl.
CPC ........... *A63B 23/04* (2013.01); *A63B 24/0087* (2013.01); *B25J 9/0006* (2013.01); *A61H 2201/018* (2013.01); *A61H 2201/0176* (2013.01); *A61H 2201/165* (2013.01); *A61H 2201/1614* (2013.01); *A61H 2201/1628* (2013.01); *A61H 2201/1642* (2013.01); *A61H 2201/1676* (2013.01); *A61H 2201/5061* (2013.01); *A61H 2201/5069* (2013.01); *A61H 2230/60* (2013.01); *A61H 2230/605* (2013.01)

(56) References Cited

U.S. PATENT DOCUMENTS

| | | |
|---|---|---|
| 5,252,102 A | 10/1993 | Singer et al. |
| 5,282,460 A | 2/1994 | Boldt |
| 5,357,424 A | 10/1994 | Kakizak et al. |
| 6,966,882 B2 | 11/2005 | Horst |
| 7,278,954 B2 | 10/2007 | Kawai et al. |
| 7,390,309 B2 | 6/2008 | Dariush |
| 7,537,573 B2 | 5/2009 | Horst |
| 7,650,204 B2 | 1/2010 | Dariush |
| 2004/0102723 A1 | 5/2004 | Horst |
| 2004/0106881 A1* | 6/2004 | McBean ............ A61B 5/04888 601/5 |
| 2004/0158175 A1 | 8/2004 | Ikeuchi et al. |
| 2006/0282022 A1 | 12/2006 | Dariush |
| 2008/0234608 A1 | 9/2008 | Sankai |

FOREIGN PATENT DOCUMENTS

| | | |
|---|---|---|
| EP | 1 842 518 A1 | 10/2007 |
| FR | 2 082 206 A5 | 11/1971 |
| JP | 05-277976 | 10/1993 |
| JP | 07-163607 | 6/1995 |
| JP | 2001-198870 | 7/2001 |
| JP | 2002-301124 | 10/2002 |
| JP | 2003-079684 | 3/2003 |
| JP | 2003-205484 | 7/2003 |
| JP | 2004-073649 | 3/2004 |
| RU | 2 271 779 C2 | 5/2005 |
| WO | 01/72245 A2 | 10/2001 |
| WO | 2004/047928 A2 | 6/2004 |

OTHER PUBLICATIONS

Patent Abstracts of Japan of JP 2004-073649 dated Mar. 11, 2004.
Patent Abstracts of Japan of JP 05-277976 dated Oct. 26, 1993.
Patent Abstracts of Japan of JP 2003-205484 dated Jul. 22, 2003.
Patent Abstracts of Japan of JP 2003-079684 dated Mar. 18, 2003.
Patent Abstracts of Japan of JP 2002-301124 dated Oct. 15, 2002.
Patent Abstracts of Japan of JP 2001-198870 dated Jul. 24, 2001.
Takao Nakai et al.,; Development of Power Assistive Leg for Walking Aid using EMG and Linux; Second Assian Symposium on Industrial Automation and Robotics, BITECH, Bangkok, Thailand, May 17-18, 2001.
Extended European Search Report dated Nov. 4, 2011 for Application No. 11176919.6-2318.
Kawai, S., et al., "A Study For Control of a Power Assist Device", Proceedings of 2004 IEEE/RSJ International Conference on Intelligent Robots and Systems, Sep. 28-Oct. 2, 2004, pp. 2283-2288.
Yamamoto, K., et al., Stand Alone Wearable Power Assisting Suit—Sensing and Control Systems, Proceedings of the 2004 IEEE International Workshop on Robot and Human Interactive Communication, Sep. 20-22, 2004, pp. 661-666.
English abstract of RU 22717799 C2.
Lee, S., et al. "Power Assist Control for Leg with HAL-3 Based on EMG and Impedance Adjustment around Knee Joint", Drafts for 20$^{th}$ Japan Robotics Conference (CD-ROM), Oct. 12, 2002, IF34.
English Translation of An Office Action of Japanese Patent Office for Japanese Patent Application 2005-018295 dated Jan. 15, 2008.

* cited by examiner

FIG.11

| | INERTIA MOMENT [kgm²] | | | COEFFICIENT OF VISCOUS FRICTION [Nm/(rad/sec)] | | GRAVITY MOMENT [Nm] | | | COULOMB FRICTION [Nm] | |
|---|---|---|---|---|---|---|---|---|---|---|
| | $J_\alpha$ | $J_\beta$ | $J_\gamma$ | $D_1$ | $D_2$ | $r_\alpha$ | $r_\beta$ | $r_\gamma$ | $C_1$ | $C_2$ |
| ACTION-ASSIST DEVICE 10 IN NON-WEARING STATE | 0.026 | 0.246 | 0.037 | 4.666 | 1.974 | 2.882 | 2.882 | 2.451 | 0.238 | 0.400 |
| WEARER A | 0.116 | 0.098 | 0.016 | 4.808 | 2.026 | 10.931 | 10.931 | 4.973 | 1.064 | 0.586 |
| WEARER B | 0.209 | 0.141 | 0.020 | 5.476 | 2.403 | 12.128 | 12.128 | 5.567 | 0.772 | 0.513 |
| WEARER C | 0.163 | 0.120 | 0.002 | 5.142 | 2.189 | 11.530 | 11.530 | 5.272 | 0.918 | 0.550 |

# WEARABLE ACTION-ASSIST DEVICE AND CONTROL PROGRAM

CROSS-REFERENCE TO RELATED APPLICATIONS

This application is a divisional of U.S. patent application Ser. No. 12/881,796 filed on Sep. 14, 2010, which is a continuation of U.S. patent application Ser. No. 11/795,907 filed Jul. 24, 2007, which is a 371 of PCT Application No. PCT/JP 2005/021472 filed on Nov. 22, 2005 which claims the benefit of priority of Japanese Patient Application No. 2005-018295 filed on Jan. 26, 2005, which are incorporated herein by reference.

TECHNICAL FIELD

This invention relates to a wearable action-assist device, and more particularly to improvement of a wearable action-assist device and its control program in which an action of a wearer is assisted or executed by substituting for the wearer.

BACKGROUND ART

In many cases, it is difficult for elderly people having muscle strength decline or physically handicapped people having lost muscle strength to perform an action or operation that can easily be performed by a healthy person. For this reason, development of various power assist devices is now in progress in order to assist or execute action of these people by substituting for them.

Among these power assist devices, there is a wearable action-assist device (which is also called action-assist device) which is put on a user (which is also called wearer), for example. Typically, the power-assist device of this kind includes a myoelectricity sensor (biosignal detection unit) which detects a myoelectricity signal accompanied with a wearer's muscular line activity, a joint angle detecting unit which detects an angular displacement of each joint of the wearer, a drive source, such as a drive motor, which supplies torque as an assisting force for the wearer, and a control unit which controls the drive source. And the power-assist device of this kind is under development. For example, see the non-patent document 1 mentioned below.

In this power-assist device, the control unit controls the drive motor suitably based on the detection result by the myoelectricity sensor and the detection result by the joint angle detecting unit. This will enable the torque conforming to the wearer's intention and suitable for the current action to be given to the wearer concerned. It is expected that this power-assist device is realized.

[Non-patent Document 1]

"Development of Power Assistive Leg for Walking Aid using EMG and Linux" by Takao Nakai, Suwoong Lee, Hiroaki Kawamoto and Yoshiyuki Sankai, Second Asian Symposium on Industrial Automation and Robotics, BITECH, Bangkok, Thailand, May 17-18, 2001.

DISCLOSURE OF THE INVENTION

Problem to be Solved by the Invention

When the above-mentioned power-assist device is put on the wearer for the first time and its initialization is performed, the kinetics parameters of the power-assist device itself, for example, the weight, the moment of inertia, and the coefficient of viscosity, are known values. However, the kinetics parameters of the wearer are unknown at that time due to change factors, such as individual differences between the individual wearers. The torque as the assisting force will be generated based on the kinetics parameters at the time of initialization, and there is a possibility that sufficient effect may not be obtained for some wearers.

Moreover, there is a case in which two or more wearers use one power-assist device by turns as in an institution where people who have declined muscle strength perform gait training or physically handicapped persons perform functional recovery training, etc. In such a case, the assumed physique of the wearer at the time of setting of the control system may differ greatly from the actual physique of each individual wearer. For this reason, there is a possibility that the setup values of the kinetics parameters of the wearer are not in conformity with the actual parameter values, and the assisting force which is originally considered to be suitable may become too small or too large for some wearers.

One may assert simply that the above-mentioned problems can be easily resolved if a dedicated power-assist device is prepared for exclusive use of every wearer. However, it is very difficult to identify the kinetics parameters of a wearer without giving physical damages, such as dissection. Moreover, even for the same wearer, the kinetics parameters may vary according to the change factors, such as physical condition and clothes. For this reason, such assertion is not appropriate.

Therefore, the above-mentioned power-assist device has a problem that sufficient effect cannot be obtained in some cases, even if various kinds of control methods are utilized in order to give the wearer the torque conforming to the wearer's intention and suitable for the current action.

Means for Solving the Problem

According to one aspect of the invention, there is provided an improved wearable action-assist device in which the above-mentioned problems are eliminated.

According to one aspect of the invention, there is provided a wearable action-assist device and its control program which can demonstrate sufficient effect in conformity with a control method without being influenced by change factors, such as an individual difference and a physical condition of the wearer.

In an embodiment of the invention which solves or reduces one or more of the above-mentioned problems, there is provided a wearable action-assist device comprising: a biosignal detection unit detecting a biosignal from a wearer; an action-assist wearing tool having a drive source supplying a torque acting on the wearer around each joint of the wearer as an axis of rotation; and a control unit controlling the drive source to generate the torque according to the biosignal detected by the biosignal detection unit, the wearable action-assist device characterized in further comprising: a drive torque estimation unit estimating a drive torque generated by the drive source; a joint angle detecting unit detecting an angular displacement of the joint; and a parameter identification unit identifying kinetics parameter concerned by substituting the estimated drive torque estimated by the drive torque estimation unit and the angular displacement detected by the joint angle detecting unit into an equation of motion of an entire system including kinetics parameters intrinsic to the wearer, wherein the control unit is configured to control the drive source according to a predetermined control method based on the equation of motion into which the biosignal detected by the biosignal detection unit and the kinetics parameters identified by the parameter identification unit are substituted.

In an embodiment of the invention which solves or reduces one or more of the above-mentioned problems, there is provided a wearable action-assist device comprising: a biosignal detection unit detecting a biosignal from a wearer; an action-assist wearing tool having a drive source supplying a torque action on the wearer around each joint of the wearer as an axis of rotation; and a control unit controlling the drive source to generate the torque according to the biosignal detected by the biosignal detection unit, the wearable action-assist device characterized in further comprising: a drive torque estimation unit estimating a drive torque generated by the drive source; a joint angle detecting unit detecting an angular displacement of the joint; a joint torque estimation unit estimating a joint torque which is a resultant of the drive torque generated by the drive source and a muscle torque generated by a muscle force of the wearer; a muscle torque estimation unit estimating a muscle torque or muscle force generated by the wearer, based on an association between the estimated drive torque estimated by the drive torque estimation unit and the estimated joint torque estimated by the joint torque estimation unit; and a parameter identification unit identifying kinetics parameter concerned by substituting the estimated drive torque estimated by the drive torque estimation unit, the angular displacement detected by the joint angle detecting unit, and the muscle torque estimated by the muscle torque estimation unit into an equation of motion of an entire system including kinetics parameters intrinsic to the wearer, wherein the control unit is configured to control the drive source according to a predetermined control method based on the equation of motion into which the kinetics parameters identified by the parameter identification unit are substituted.

The above-mentioned wearable action-assist device may be configured to further comprise a calibration unit adjusting a gain between a biosignal detected by the biosignal detection unit and a muscle torque or muscle force estimated by the muscle torque estimation unit, so that an association between the biosignal and the muscle torque or muscle force is in conformity with a predetermined association.

The above-mentioned wearable action-assist device may be configured so that the biosignal detection unit is used in a state where the biosignal detection unit is stuck on a skin of the wearer, and the biosignal detection unit detecting a myoelectricity of the wearer as the biosignal.

The above-mentioned wearable action-assist device may be configured so that the action-assist wearing tool includes a waist belt, a right leg auxiliary part extending downward from a right side part of the waist belt, and a left leg auxiliary part extending downward from a left side part of the waist belt, and each of the right leg auxiliary part and the left leg auxiliary part comprising: a first frame extending downward to support the waist belt; a second frame extending downward from the first frame; a third frame extending downward from the second frame; a fourth frame provided at a lower end of the third frame as that a sole of the foot of the wearer is placed on the fourth frame; a first joint provided between a lower end of the first frame and an upper end of the second frame, and a second joint provided between a lower end of the second frame and an upper end of the third frame.

The above-mentioned wearable action-assist device may be configured so that the first joint is disposed in a height position which is equivalent to that of a hip joint of the wearer, the first joint comprises a first drive source transmitting a drive force to rotate the second frame, and a first joint angle detecting unit detecting an angular displacement of the hip joint of the wearer, and the second joint is disposed in a height position which is equivalent to that of a knee joint of the wearer, and the second joint comprises a second drive source transmitting a drive force to rotate the third frame, and a second joint angle detecting unit detecting an angular displacement of the knee joint of the wearer.

The above-mentioned wearable action-assist device may be configured so that the control unit is configured to control the drive source according to a control method using the kinetics parameters identified by the parameter identification unit and performing at least one of gravity compensation and inertia compensation.

The above-mentioned wearable action assist device may be configured so that the control unit is configured to control the drive source according to an impedance control method using the kinetics parameters identified by the parameter identification unit.

In an embodiment of the invention which solves or reduces one or more of the above-mentioned problems, there is provided a control program which, when executed by a computer acting as the control unit, causes the computer to perform the above-mentioned control method.

In an embodiment of the invention which solves or reduces one or more of the above-mentioned problems, there is provided a control program which, when executed by a computer acting as the control unit, causes the computer to perform the above-mentioned control method.

EFFECTS OF THE INVENTION

According to embodiments of the wearable action-assist device of the invention, in the state where a wearer wears the action-assist device, the kinetics parameters intrinsic to the wearer concerned are identified by a parameter identification unit. And the drive source can be controlled by the control unit based on the equation of motion into which the identified kinetics parameters are substituted. It is possible to demonstrate sufficient effect in conformity with the control method used by the control unit, without being influenced by the change factors, such as wearer's individual difference and physical condition.

Moreover, according to the embodiments of the invention, the drive source can be controlled by the control unit based on the equation of motion into which the muscle torque or muscle force estimated by the muscle torque estimation unit is further substituted. The kinetics parameters can be identified even in the state where a muscle force is produced by the wearer, and the above-mentioned effect can be demonstrated without taking the latency time for identifying the kinetics parameters.

Moreover, according to the embodiments of the invention, the wearable action-assist device further comprises a calibration unit adjusting a gain between a biosignal detected by the biosignal detection unit and a muscle torque or muscle force estimated by the muscle torque estimation unit, so that an association between the biosignal and the muscle torque or muscle force is in conformity with a predetermined association. It is possible to avoid the occurrence of poor sensitivity or oversensitivity due to the detection result received from the biosignal detection unit. As a result, it is possible to avoid the situation where the identification accuracy of the kinetics parameters of the wearer falls, and it is possible to avoid the situation where the assisting force generated by the drive source becomes too small or too large.

Moreover, according to the embodiments of the invention, the control unit is configured to control the drive source according to a control method using the kinetics parameters identified by the parameter identification unit and performing at least one of gravity compensation and inertia compensation. It is possible to suppress the situation where the weight of the action-assist device gives the wearer sense of burden, and the situation where the inertia of the action-assist device gives the wearer sense of incongruity at the time of operation.

Moreover, according to the embodiments of the invention, the control unit is configured to control the drive source according to an impedance control method using the kinetics parameters identified by the parameter identification unit. It is possible to demonstrate sufficient effect in conformity with the impedance control method in which the apparent inertia, the apparent viscosity, etc. of the action-assist device are reduced so as to realize light operation.

BRIEF DESCRIPTION OF THE DRAWINGS

FIG. 11 is a diagram showing the experimental result at the time of conducting an identification experiment under the same conditions for each of the tested persons A, B, and C as the wearer 12.

Figure 1:
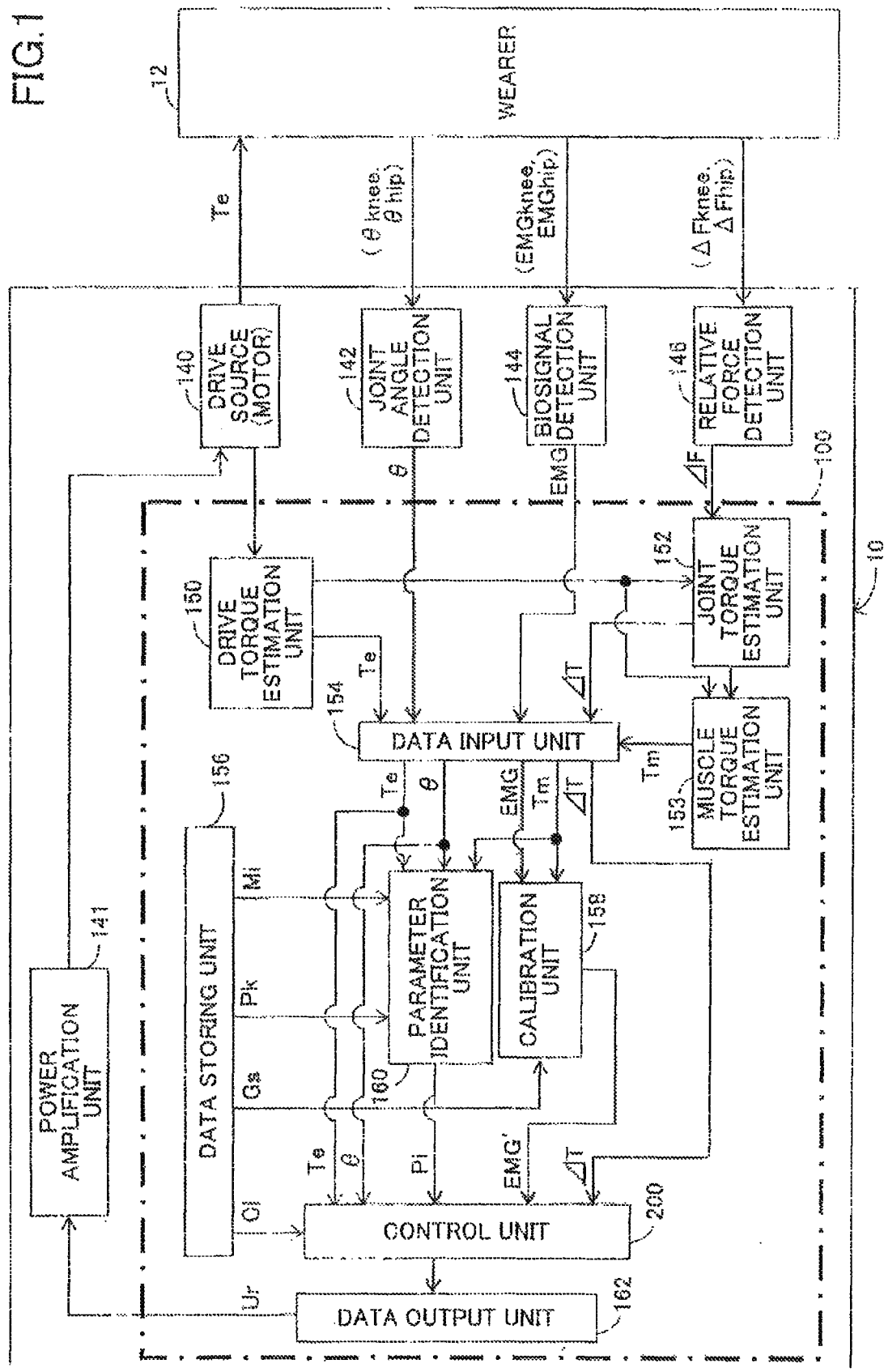
FIG. 1 is a block diagram showing the composition of a control system of a wearable action-assist device in an embodiment of the invention.

DESCRIPTION OF NOTATIONS 10 action-assist device
12 wearer
20 right thigh drive motor
22 left thigh drive motor
24 right knee drive motor
26 left knee drive motor
30 waist belt
32, 34 batteries
36 control back
38a, 38b, 40a, 42a, 42b, 44a, 44b myoelectricity sensors
45, 46 force sensors
50a, 50b, 52a, 52b reaction force sensors
54 right leg auxiliary part 55 left leg auxiliary part
56 first frame
58 second frame
60 third frame
62 fourth frame
64 first joint
66 second joint
70, 72, 74, 76 angle sensors
78 first fastening belt
80 second fastening belt
84 heel receptacle part
100 control device
140 drive source
142 joint angle detection unit
144 biosignal detection unit
146 relative force detection unit
150 drive torque estimation unit
152 joint torque estimation unit
153 muscle torque estimation unit
154 data input unit
156 data storing unit
158 calibration unit
160 parameter identification unit
162 data output unit
200 control unit
18 action-assist wearing tool
68 motor bracket
68a motor supporting unit
141 power amplification unit

BEST MODE FOR CARRYING OUT THE INVENTION

A description will now be given of embodiments of the invention with reference to the accompanying drawings.

EMBODIMENTS

FIG. 1 shows the composition of a control system of a wearable action-assist device in an embodiment of the invention.

As shown in FIG. 1, the wearable action-assist device 10 includes a drive source 140 which supplies an assisting force to a the wearer 12, a joint angle detecting unit 142 which detects an angular displacement θ of each joint of the wearer 12, a biosignal detection unit 144 which detects a myoelectricity signal (biosignal) according to the muscle force generated by the wearer 12, and a relative force detection unit 146 which detects a relative force ($\Delta F$) acting on the action-assist device 10.

Figure 2:
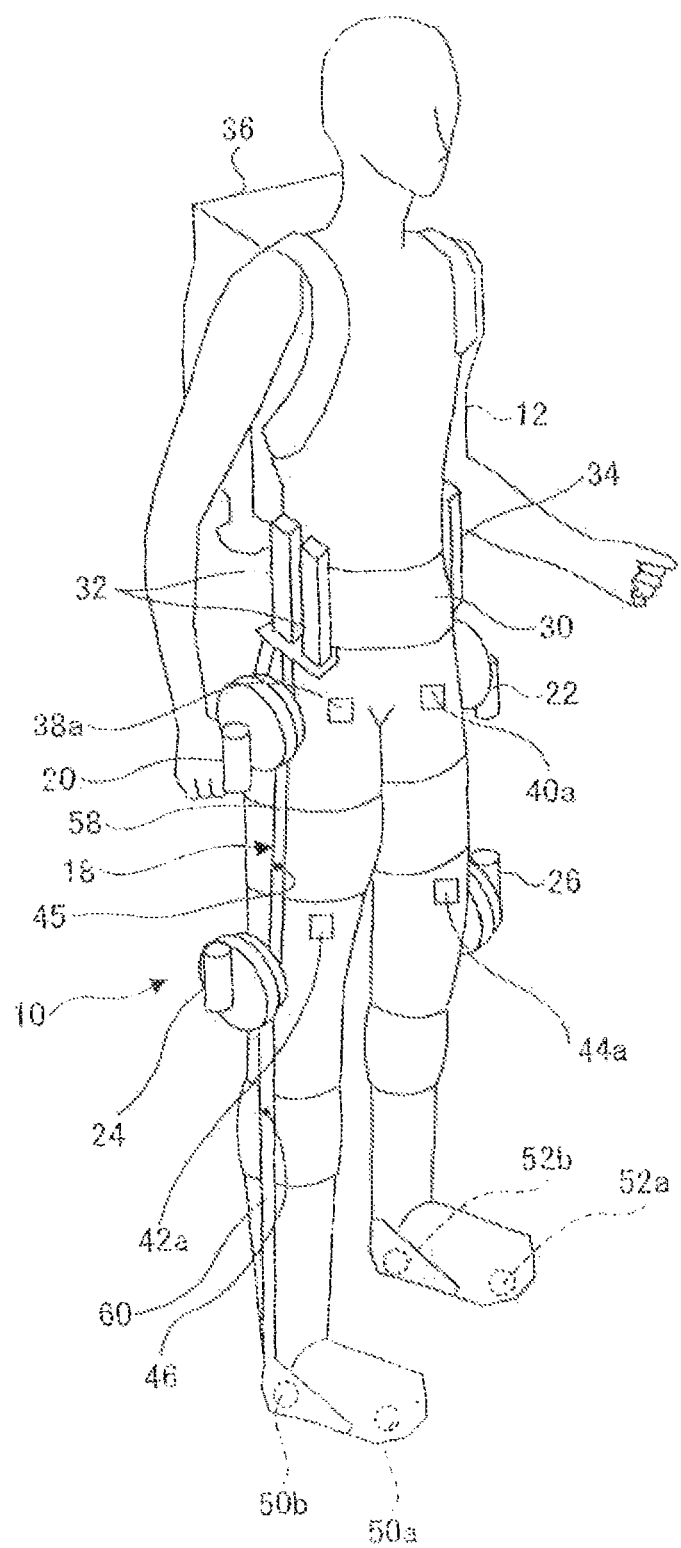
FIG. 2 is a perspective view of the wearable action-assist device of this embodiment, when viewed from the front side, in the state where the action-assist device is put on the wearer.
Figure 3:
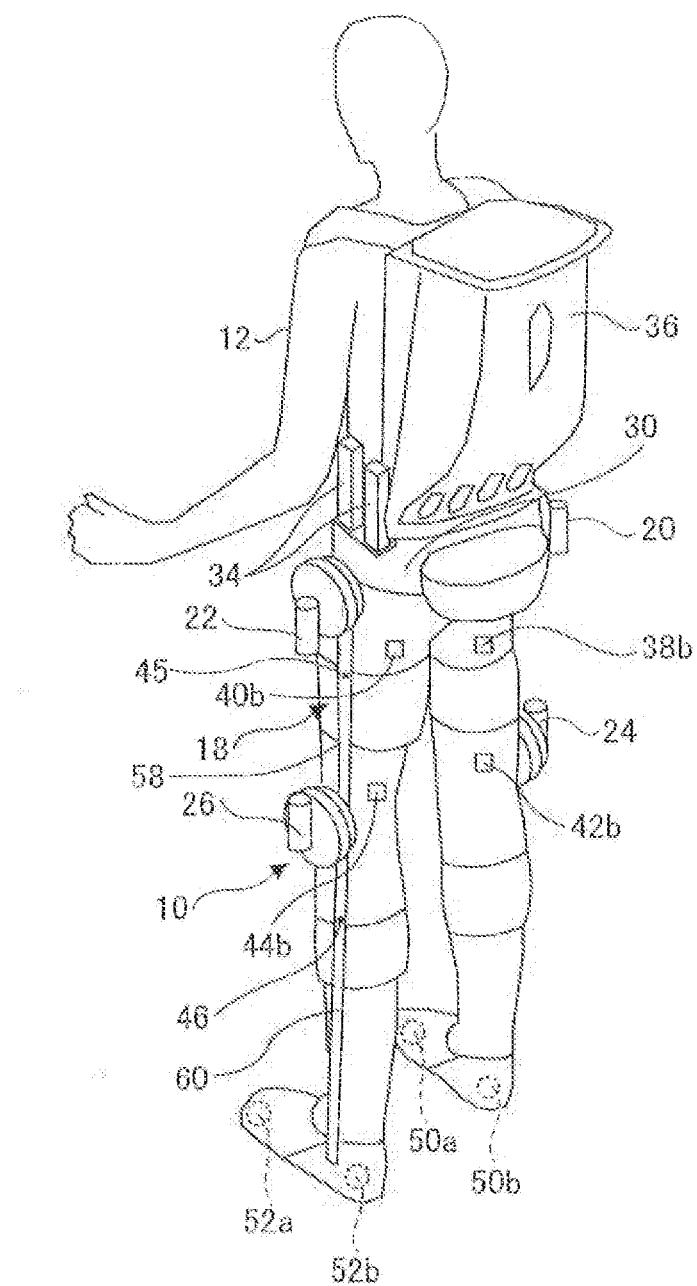
FIG. 3 is a perspective view of the wearable action-assist device of this embodiment, when viewed from the back side, in the state where the action-assist device is put on the wearer.

This assisting force is to create the torque acting on the wearer around each joint of an action-assist wearing tool 18 shown in FIG. 2 and FIG. 3 (equivalent to each of knee joints and a hip joint of the wearer 12) as the axis of rotation. The assisting force may also be mentioned as assisting torque.

The relative force which is determined relatively depending on the relation between the forces acting on the frame of the action-assist wearing tool 18 (i.e., the force generated by the drive source 140 and the muscle force generated by the wearer 12).

The action-assist device 10 further includes a control device 100 which carries out drive control of the drive source 140 through a power amplification unit 141. The control device 100 includes a drive torque estimation unit 150, a joint torque estimation unit 152, a muscle torque estimation unit 153, a data input unit 154, a data storing unit 156, a calibration unit 158, a parameter identification unit 160, a control unit 200, and a data output unit 162.

The drive torque estimation unit 150 estimates a drive torque Te which is generated by the drive source 140. For example, the drive torque estimation unit 150 may use a drive torque estimation method in which a current value supplied to the drive source 140 is detected, and estimation of the drive torque (Te) is performed by multiplying the detected current value by a given torque constant intrinsic to the drive source 140.

The joint torque estimation unit 152 estimates a joint torque ($\Delta T$) acting on the wearer 12 around each joint of the wearer 12, according to the relative force ($\Delta F$) detected by the relative force detection unit 146.

Figure 8A:
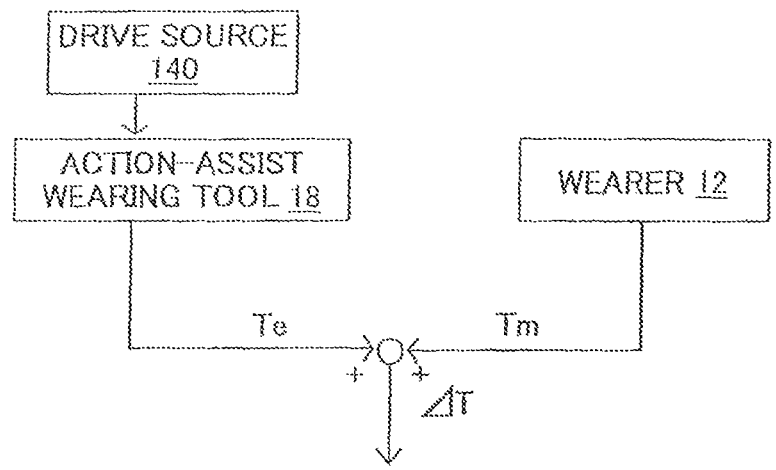
FIG. 8A is a diagram showing an action with the assisting force of the drive source 140 and the muscle force of the wearer 12, which shows that the resultant of the drive torque (Te) of the drive source 140 and the muscle torque (Tm) of the wearer 12 acts as a joint moment ($\Delta T$).

The muscle torque estimation unit 153 estimates a muscle torque ($\Delta Tm$) generated by the muscle force of the wearer 12, based on the drive torque (Te) estimated by the drive torque estimation unit 150 and the joint torque ($\Delta T$) estimated by the joint torque estimation unit 152 (refer to FIG. 8A).

The data input unit 154 provides an input interface of the detected data from the detection units and the estimated data from the estimation units in the action-assist device 10. The data needed for performing various operation processing in the control device 100 are stored in the data storing unit 156. The calibration unit 158 reads, from the data input unit 154, the detected myoelectricity (EMG) and the estimated muscle force (F') and reads a predetermined setting gain (Gs) from the data storing unit 156. And the calibration unit 158 adjusts a gain between the detected myoelectricity and the estimated myoelectricity (EMG) and the estimated muscle force (F') is in conformity with the setting gain (Gs).

The parameter identification unit 160 is provided to constitute an equation of motion of a target system on the operation environment therein by using the motion equation data (Mi) and the known parameter (Pk) (which will be mentioned later) read from the data storing unit 156. And the parameter identification unit 160 is provided to enable substitution of the estimated drive torque (Te), the estimated joint torque ($\Delta T$), and the joint angle (θ), received from the data input unit 154, into the equation of motion concerned.

The parameter identification unit 160 is provided to identify the kinetics parameters (which will become unknown in the equation of motion concerned) by substituting the data from the data input unit 154 into the equation of motion concerned. This will be described in greater detail later.

The control unit 200 is provided to read the control method data (Ci) (which will be described below) from the data storing unit 156, and read the estimated drive torque (Te), the estimated joint torque ($\Delta T$) and the joint angle (θ) from the data input unit 154. Moreover, the control unit 200 is provided to read the identified parameters (Pi) from the parameter identification unit 160, and read the corrected myoelectricity (EMG') from the calibration unit 158.

The control unit 200 is provided to constitute a predetermined control mechanism on the operation environment therein by using the control method data (Ci). The control unit 200 substitutes the estimated drive torque (Te), the estimated joint torque ($\Delta T$), the joint angle (θ), the identified parameters (Pi) and the corrected myoelectricity (EMG') into the above-mentioned control mechanism, so that a control signal Ur which is provided to control the drive source 140 can be outputted to the data output unit 162. This will be described in greater detail later.

The data output unit 162 serves as an output interface which outputs the control signal Ur received from the control unit 200, to the power amplification unit 141. The power amplification unit 141 drives the drive source 140 according to the control signal Ur received from the data output unit 162.

The calibration unit 158, the parameter identification unit 160 and the control unit 200 as mentioned above may be provided on a CPU (central processing unit). If they are constituted on a single CPU collectively, miniaturization of the device and reduction of the component parts will be realized.

FIG. 2 is perspective view of the wearable action-assist device of this embodiment, when viewed from the front side, in the state where the action-assist device is put on the wearer. FIG. 3 is a perspective view of the wearable action-assist device of this embodiment, when viewed from the back side, in the state where the action-assist device is put on the wearer.

As shown in FIG. 2 and FIG. 3, the action-assist device 10 is designed to assist a walking action of a wearer who may be a leg-motion disabled person having a difficulty in a walk action due to the loss of muscle strength of skeletal muscle, or a patient who is difficult to walk by himself and performs rehabilitation of a walking operation. This action-assist device 10 is provided to detect a biosignal (surface myoelectricity) accompanied with a muscle force generated according to a signal from the brain, and the action-assist device 10 controls the drive source 140 (in this embodiment, an electromotive drive motor is used) based on the detected biosignal, so that the wearer is supplied with an assisting force of the drive source.

Therefore, the action-assist device 10 is quite different from a so-called played-back type robot which is provided to perform a computer-aided control of a robot hand based on the data inputted beforehand. The action-assist device 10 is called a robot suit or a powered suit.

If the wearer 12 who puts on the action-assist device 10 operates with his intention, the wearer 12 is supplied with an assisting force of the action-assist device 10 which is produced according to the biosignal at that occasion, and can walk according to the resultant of the assisting force concerned and his own muscle force. For example, if the assisting force is equivalent to half of the resultant concerned, it enables the wearer 12 to operate with the half of the necessary muscle force.

Next, the composition of the action-assist device 10 of this embodiment will be explained.

As shown in FIG. 2 and FIG. 3, the action-assist device 10 includes the action-assist wearing tool 18 which is attached to the wearer 12, and the drive source 140 is provided in the action-assist wearing tool 18. Specifically, the action-assist wearing tool 18 includes a right thigh drive motor 20 located at the right hip joint of the wearer 12, a left thigh drive motor 22 located at the left hip joint, a right knee drive motor 24 located at the right knee joint, and a left knee drive motor 26 located at the left knee joint, respectively.

These drive motors 20, 22, 24 and 26 are equivalent to the drive source 140 mentioned above. Specifically, these drive motors are servo motors each supplying a drive torque controlled by the command signal from the control device 100, and containing the deceleration mechanism (not shown) which slows down the motor rotation by a predetermined reduction ratio.

Batteries 32 and 34 are attached to a waist belt 30 which is put on the waist of the wearer 12, and these batteries function as a power supply for driving the drive motors 20, 22, 24 and 26. The batteries 32 and 34 are rechargeable batteries, and the mounting positions of them are distributed to right and left so that a walk action of the wearer 12 may not be barred.

In a control back 36 which is put on the back of the wearer 12, the control equipment, including the power amplification unit 141, the control device 100, and the power supply circuit (not shown), is accommodated. The lower part of the control back 36 is supported by the waist belt 30, and it is provided so that the weight of the control back 36 may not become a burden of the wearer 12.

Moreover, the action-assist device 10 includes myoelectricity sensors 38a and 38b which detect a myoelectricity (EMGhip) accompanied with a motion of the right thigh of the wearer 12, myoelectricity sensors 40a and 40b which detect a myoelectricity (EMGhip) accompanied with a motion of the left thigh of the wearer 12, myoelectricity sensors 42a and 42b which detect a myoelectricity (EMGknee) accompanied with a motion of the right knee of the wearer 12, and myoelectricity sensors 44a and 44b which detect a myoelectricity (EMGknee) accompanied with a motion of the left knee of the wearer 12. Each of these myoelectricity sensors 38a, 38b, 40a, 40b, 42a, 42b, 44a, and 44b is equivalent to the biosignal detection unit 144 mentioned above. Specifically, these sensors are detection units which measure the surface myoelectricity accompanied when the skeletal muscle generates a muscle force, and each of these sensors includes an electrode (not shown) which detects a very small potential generated in the skeletal muscle.

In this embodiment, each of the myoelectricity sensors 38a, 38b, 40a, 40b, 42a, 42b, 44a and 44b is stuck on a skin of the wearer 12 with an adhesion seal which covers the circumference of the electrode.

The principle that the action-assist device 10 in which these myoelectricity sensors are provided supplies the wearer 12 with an assisting force in conformity with the optional intention of the wearer 12 will be described.

In a human body, the acetylcholine of a synaptic transmitter is emitted to the surface of the muscles which form the skeletal muscle, by the instructions from the brain. As a result, the ion permeability of the muscular fiber film changes, and the action potential (EMG: Electro MyoGram Myoelectricity) occurs. And with the action potential, contraction of the muscular fiber occurs and a muscle force is generated. Therefore, by detecting the myoelectricity of the skeletal muscle, estimating a muscle force produced in the case of a walk action is possible, and determining an assisting force required for the walk action from a virtual torque based on the estimated muscle force is possible.

Muscles are expanded and contracted if the proteins called action and myosin are supplied with blood, but a muscle force is created only when the muscles are contracted. Therefore, at a joint where two bones are connected with each other in a mutually rotatable state, the flexor muscle which generates a force in the bending direction of the joint, and the extensor muscle which generates a force in the elongating direction of the joint are provided between the two bones. And the human body has a plurality of muscles that are located below the waste to move the legs, including the iliopsoas muscle which raises the thigh, the gluteous maximus which lowers the thigh, the quadriceps femoris which elongates the knee, the biceps femoris which bends the knee, etc.

The myoelectricity sensors 38a and 40a mentioned above are stuck on the front parts of the root portions of the thighs of the wearer 12. Each sensor can detect the surface myoelectricity of the iliopsoas muscle and can measure the myoelectricity according to the muscle force when the leg is moved forward.

The myoelectricity sensors 38*b* and 40*b* are stuck on the hip parts of the wearer 12. Each sensor can detect the surface myoelectricity of the gluteus maximus and can measure the myoelectricity according to the muscle force, when the wearer goes up the stairs or kicks back.

The myoelectricity sensors 42*a* and 44*a* are stuck on the front parts above the knees of the wearer 12. Each sensor can detect the surface myoelectricity of the quadriceps femoris and can measure the myoelectricity according to the muscle force to put forward the lower part of the knee.

The myoelectricity sensors 42*b* and 44*b* are stuck on the back parts above the knees of the wearer 12. Each sensor can detect the surface myoelectricity of the biceps femoris and can measure the myoelectricity according to the muscle force to return the lower part of the knee.

Thus, according to the action-assist device 10 in which the myoelectricity sensors 38*a*, 38*b*, 40*a*, 40*b*, 42*a*, 42*b*, 44*a* and 44 are provided, the myoelectricity according to activity of any of the iliopsoas muscle, the gluteus maximus, the quadriceps femoris and the biceps femoris can be detected. And the drive motors 20, 22, 24 and 26 are driven by the drive current according to the myoelectricity concerned, thereby attaining the supply of the assisting force in conformity with the optional intention of the wearer 12 to the wearer 12.

Moreover, the action-assist wearing tool 18 in the action-assist device 10 includes a force sensor 45 which detects the torque acting around the hip joint of the wearer 12, and a force sensor 46 which detects the torque acting around the knee joint of the wearer 12. These sensors are equivalent to the relative force detection unit 146 mentioned above. For example, each of the force sensors 45 and 46 includes a strain gage which detects a distortion according to the applied force and outputs an electric signal proportional to the magnitude of the distortion. The force sensors 45 and 46 are disposed at the right leg part and the left leg part of the action-assist wearing tool 18.

Specifically, the force sensor 45 is disposed in the position of the second frame 58, corresponding to the thigh part of the wearer 12, which is subjected to distortion due to the bending by the drive torque of the drive motors 20 and 22. The force sensor 46 is disposed in the position of the third frame 60, corresponding to the knee part of the wearer 12, which is subjected to distortion due to the bending by the drive torque of the drive motors 24 and 26.

Moreover, in order to perform smooth movement of the center of gravity during a walk action or the like, it is necessary for the action-assist device 10 to detect the load acting on the sole of the foot. In this embodiment, reaction force sensors 50*a*, 50*b*, 52*a* and 52*b* (indicated by the dotted lines in FIG. 2 and FIG. 3) are disposed at the sole parts of the right and left feet of the wearer 12.

Specifically, the reaction force sensor 50*a* detects a reaction force to the load acting on the front side of the right leg, and the reaction force sensor 50*b* detects a reaction force to the load acting on the back side of the right leg. The reaction force sensor 52*a* detects a reaction force to the load acting on the front aide of the left leg, and the reaction force sensor 52*b* detects a reaction force to the load on the back side of the left leg. For example, each of the reaction force sensors 50*a*, 50*b*, 52*a* and 52*b* includes a piezoelectric element which outputs a voltage according to the applied load. With the reaction force sensors, it is possible to detect a load change accompanied with a weight shift, and detect whether the leg of the wearer 12 is in contact with the ground.

Next, the composition of the action-assist wearing tool 18 will be explained with reference to FIGS. 4 and 5.

Figure 4:
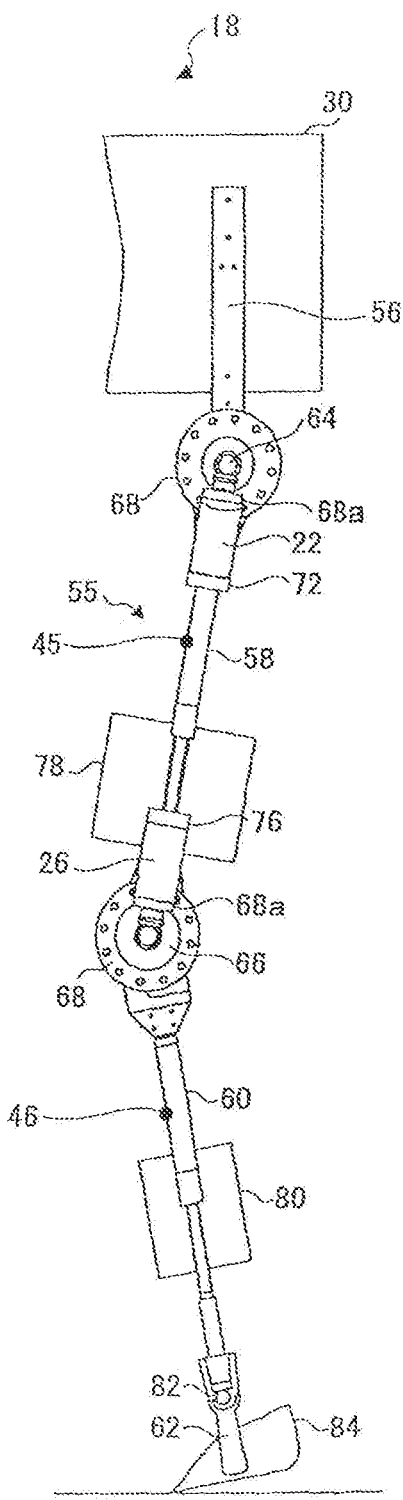
FIG. 4 is a left side view of an action-assist wearing tool 18.

FIG. 4 is a left side view of the action-assist wearing tool 18. FIG. 5 is a rear elevation of the action-assist wearing tool 18.

Figure 5:
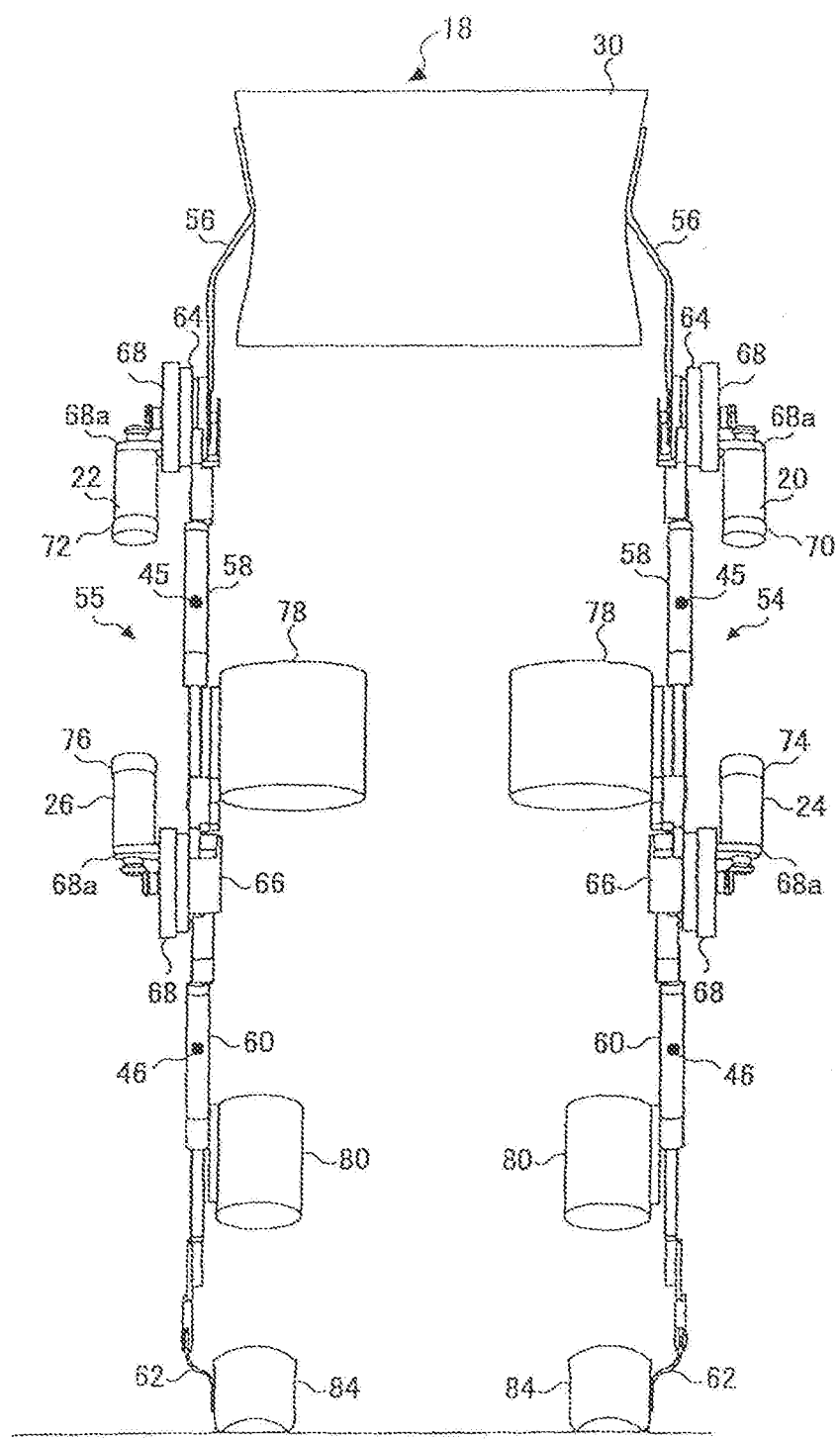
FIG. 5 is a rear elevation of the action-assist wearing tool 18.

As shown in FIG. 4 and FIG. 5, the action-assist wearing tool 18 includes the waist belt 30 which is put on the waist of the wearer 12, a right leg auxiliary part 54 extending downward from the right side part of the waist belt 30, and a left leg auxiliary part 55 extending downward from the left leg side part of the waist belt 30.

The right leg auxiliary part 54 and the left leg auxiliary part 55 are arranged symmetrically to each other. Each auxiliary part includes a first frame 56 extending downward from the waist belt 30 and supporting the waist belt 30, a second frame 58 extending downward from the first frame 56 along the outside of the thigh of the wearer 12, a third frame 60 extending downward from the second frame 58 along the outside of the knee of the wearer 12, and a fourth frame 62 provided at the lower end of the third frame 60 in which the sole of the foot of the wearer 12 (which, when wearing a shoe, is the bottom of the shoe) is laid.

A first joint 64 having a bearing structure is provided between the lower end of the first frame 56 and the second frame 58, so that the first frame 56 and the second frame 58 are connected together to be mutually rotatable. This first joint 64 is disposed in a height position which is equivalent to that of the hip joint of the wearer. The first frame 56 is secured to the fixed support side of the first joint 64, and the second frame 58 is secured to the rotatable side of the first joint 64.

A second joint 66 having a bearing structure is provided between the lower end of the second frame 58 and the third frame 60, so that the second frame 58 and the third frame 60 are connected together to be mutually rotatable. The second joint 66 is disposed in a height position which is equivalent to that of the knee joint of the wearer. The second frame 58 is secured to the fixed support side of the second joint 66, and the third frame 60 is secured to the rotatable side of the second joint 66.

Therefore, the second frame 58 and the third frame 60 are provided so as to perform pendulum movement to the first frame 56 (fixed to the waist belt 30) around the first joint 64 and the second joint 66 as the rotation fulcrums. Namely, they are constituted so that the second frame 58 and the third frame 60 are movable in the same manner as the operation of the legs of the wearer 12.

And a motor bracket 68 is provided on the support side of each of the first joint 64 and the second joint 66. The motor bracket 68 includes a motor supporting unit 68*a* projecting in the outward horizontal direction. The drive motors 2, 22, 24 and 26 are contained in the motor supporting units 68*a* of the motor brackets 68 in the vertical attitude. Therefore, the drive motors 20, 22, 24 and 26 are not projecting sidewise excessively, and they are provided so as to avoid contact with a surrounding obstacle or the like when the wearer walks.

At the first joint 64 and the second joint 66, the rotation shafts of the drive motors 20, 22, 24 and 26 transmit the drive torque to the second frame 58 and the third frame 60 via the engaging gears, so that the second frame 58 and the third frame 60 are supplied with the drive torque.

Moreover, the drive motors 20, 22, 24 and 26 include have angle sensors 70, 72, 74 and 76 each of which detects a joint angle. Each of these angle sensors is equivalent to the joint angle detecting unit 142 mentioned above. For example, each of the angle sensors 70, 72, 74 and 76 includes a rotary encoder which counts the number of pulses proportional to a joint angle of one of the first joint 64 and the second joint 66 and output an electric signal according to the counted pulse number (proportional to the joint angle) as a sensor output.

The angle sensors 70 and 72 detect a rotation angle between the first frame 56 and the second frame 58, equivalent to the joint angle (θ hip) of the hip joint of the wearer 12. The angle sensors 74 and 76 detect a rotation angle between the lower end of the second frame 58 and the third frame 60, equivalent to the joint angle (θ knee) of the knee joint of the wearer 12.

The first joint 64 and the second joint 66 are provided so that they are rotatable only in the angle range where the hip joint and knee joint of the wearer 12 are rotatable, and the stopper mechanism (not shown) is provided therein so as to avoid giving an impossible motion to the hip joint and knee joint of the wearer 12.

A first fastening belt 78 which is fastened to the thigh of the wearer 12 is attached to the second frame 58. A second fastening belt 80 which is fastened to the part under the knee of the wearer 12 is attached to the third frame 60. Therefore, the drive torque generated by the drive motors 20, 22, 24 and 26 are transmitted to the second frame 58 and the third frame 60 via the gears, and it is further transmitted to each leg of the wearer 12 as the assisting force via the first fastening belt 78 and the second fastening belt 80.

The fourth frame 62 is connected to the lower end of the third frame 60 via a shaft 82 in a rotatable manner. A heel receptacle part 84 in which the heel part of the sole of the foot of the wearer 12 is laid is provided at the lower end of the fourth frame 62. And the length of the second frame 58 and the third frame 60 in the longitudinal direction is adjustable by a screw mechanism, so that the length may be adjusted to an arbitrary length in conformity with the length of the leg of the wearer 12 by using the screw mechanism.

Each of the frames 56, 58, 60, and 64 is made of a metal respectively, and these frames can support the weight of the batteries 32 and 34 provided in the waist belt 30, the control back 36, and the action-assist wearing tool 18. Namely, the action-assist device 10 is provided so that the weight, including the action-assist wearing tool 18, may not act on the wearer 12 and excessive load may not be given to the wearer 12.

Next, the procedure of an assist control processing which is performed by the control device 100 when the wearer 12 wears the above-mentioned action-assist wearing tool 18 and performs a walk action will be explained with reference to FIG. 6.

Figure 6:
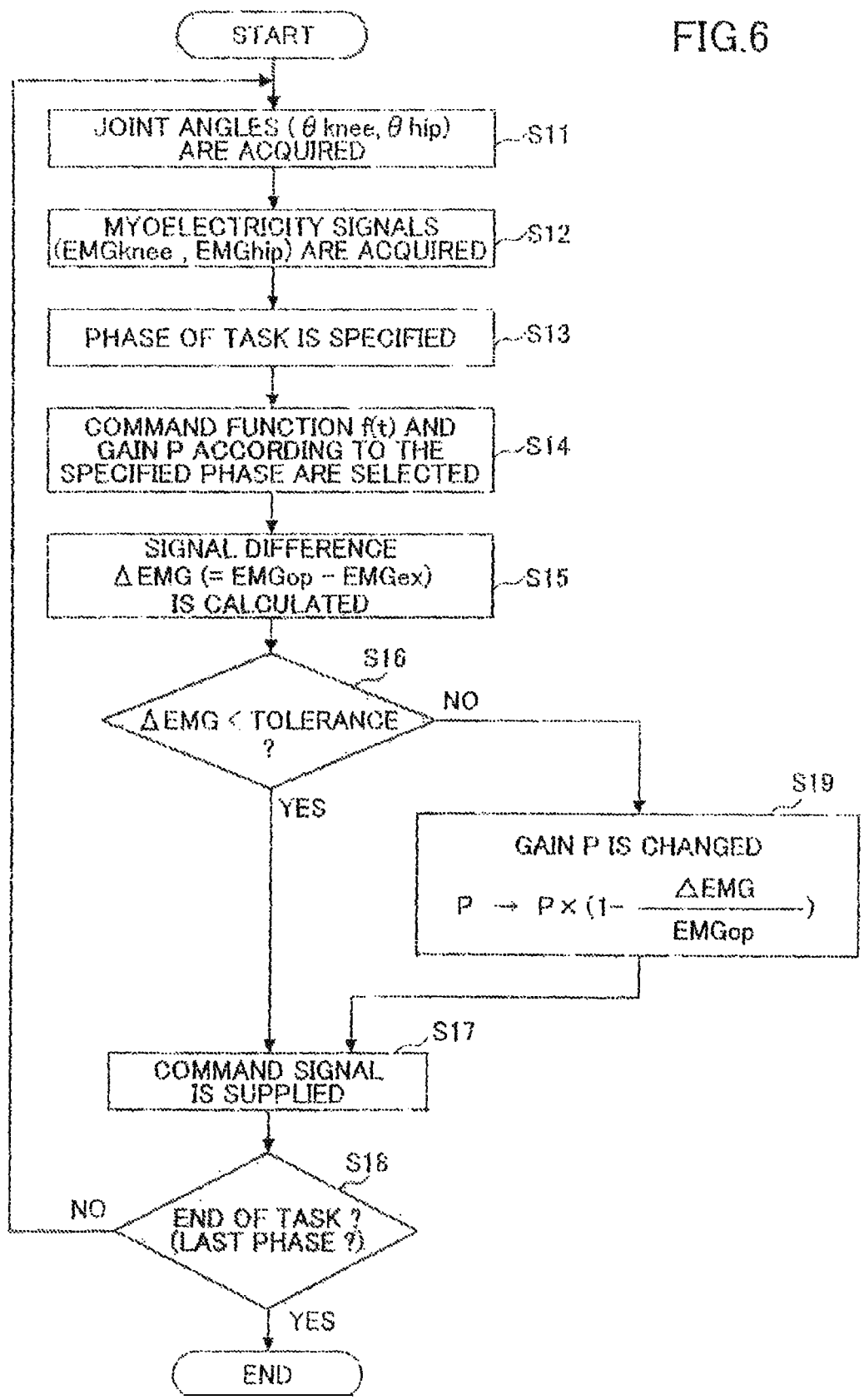
FIG. 6 is a flowchart for explaining the procedure of an action-assist control processing performed by a control device 100.

As shown in FIG. 6, upon start of the procedure, the control device 100 acquires at step S11 the joint angles (θknee, θhip) detected by the angle sensors 70, 72, 74, and 76, which are equivalent to the joint angle detecting unit 142.

Progressing to step S12, the control device 100 acquires the myoelectricity signals (EMGknee, EMGhip) detected by the myoelectricity sensors 38*a*, 38*b*, 40*a*, 40*b*, 42*a*, 42*b*, 44*a* and 44*b*, which are equivalent to the biosignal detection unit 144.

Progressing to step S13, the control device 100 compares the joint angles (θknee, θhip) and the myoelectricity signals (EMGknee, EMGhip), acquired in the steps S11 and S12, with the reference parameters from a reference parameter database (not shown). The control device 100 specifies the phase of the task corresponding to the action of the wearer 12.

At the following step S14, the control device 100 selects a command function f (t) and a gain P according to the phase specified in the step S13 (autonomous control unit).

And, progressing to step S15, a signal difference (ΔEMG) between the biosignal (EMGop) of the reference parameter corresponding to the joint angle detected by the joint angle detection unit 142, and the myoelectricity signal (EMGex) detected by the biosignal detection unit 144 is calculated according to the formula ΔEMG (=EMGop-EMGex) (determination unit).

At the following step S16, the different ΔEMG calculated in the above step S15 is compared with a predetermined tolerance (threshold) and it is determined whether the difference ΔEMG is less that the tolerance.

When the difference ΔEMG is less than the tolerance at step S16, the myoelectricity to the joint action of the wearer 12 corresponds to the action of the wearer 12. It is judged that the drive torque from the drive motors 20, 22, 24 and 26 equivalent to the drive source 140 can be given to the leg of the wearer 12 as the assisting force.

Therefore, when the difference ΔEMG is less than the tolerance at step S16, a command signal is transmitted to the motor driver (not shown) equivalent to the power amplification unit 141 (S17). Thereby, the drive motors 20, 22, 24 and 26 which are equivalent to the drive source 140 generate the drive torque based on the joint angles (θ knee, θ hip) and the myoelectricity signals (EMGknee, EMGhip) acquired from the wearer 12. This drive torque is transmitted to the leg of the wearer 12 as the assisting force via the second frame 58, the third frame 60, the first fastening belt 78 and the second fastening belt 80.

When the difference ΔEMG exceeds the tolerance at step S16, the myoelectricity to the joint action of the wearer 12 does not correspond to the action of the wearer 12. It is judged that the drive torque from the drive motors 20, 22, 24 and 26 does not correspond to the motion which the wearer 12 intends to perform.

Therefore, when the difference ΔEMG exceeds the tolerance at step S16, the change processing of the gain P is performed at step S19. Namely, at step S19, a corrected gain P'=P×{1−(ΔEMG/EMGop)} is calculated, and the gain P is changed to the corrected gain P' (<P).

And at step S17, the command signal (control signal) generated with the corrected gain P' in this case has a value smaller than that in the case of gain P, and the control signal which is smaller than that in the case of gain P is supplied to the motor driver (not shown) equivalent to the power amplification unit 141. Thereby, the drive motors 20, 22, 24 and 26 generate a drive torque which is smaller than that in the case of gain P.

As a result, the drive motors 20, 22, 24 and 26 generate the drive torque based on the actual measurements of the myoelectricity signals (EMGknee, EMGhip) which are in conformity with the intention of the wearer 12, regardless of the phase of each action. This drive torque is transmitted to the leg of the wearer 12 as the assisting force via the second frame 58, the third frame 60, the first fastening belt 78 and the second fastening belt 80.

In this manner, the change processing of gain P is performed at the step S19. Thus, even when the wearer 12 stops a certain action intermittently and changes the action (phase) into another action (phase), the assisting force can be decreased as soon as the myoelectricity signal from the wearer 12 falls, and it is possible to avoid forcing the wearer 12 to perform the initial operation against the intention of the wearer 12 in such cases.

Therefore, the wearer 12 can acquire the assisting force in conformity with the intention of the wearer 12 in accordance with the above-described control method in which the autonomous control and the pseudo-optional control approximated to the optional control, are performed in a mixed manner.

At the following step S18, it is determined whether the action-assist control processing for the last phase of the task concerned is completed. When the action-assist control processing for the last phase of the task concerned remains incomplete at step S18, the control is returned to the above-mentioned step S11 and the action-assist control processing (S11-S18) for the next phase will be performed. When the action-assist control processing for the last phase of the task concerned is completed at step S18, this procedure of the action-assist control processing is ended.

Next, the motion equation data (Mi) and the known parameters (Pk) which are read from the data storing unit 156 into the parameter identification unit 160 will be explained. The motion equation data (mi) are provided to constitute the equation of motion of the entire system including the action-assist device 10 and the wearer 12. The known parameters (Pk) include the kinetics parameters, much as the weight of each part of the action-assist device 10, the moment of inertia around each joint, the coefficient of viscosity, and the Coulomb friction coefficient. This equation of motion relates to the entire system including the action-assist device 10 and the wearer 12, and it is expressed, for example, by the model shown in FIG. 7A, FIG. 7B, FIG. 8A, FIG. 8B and the formula (1) mentioned below.

Figure 7A:
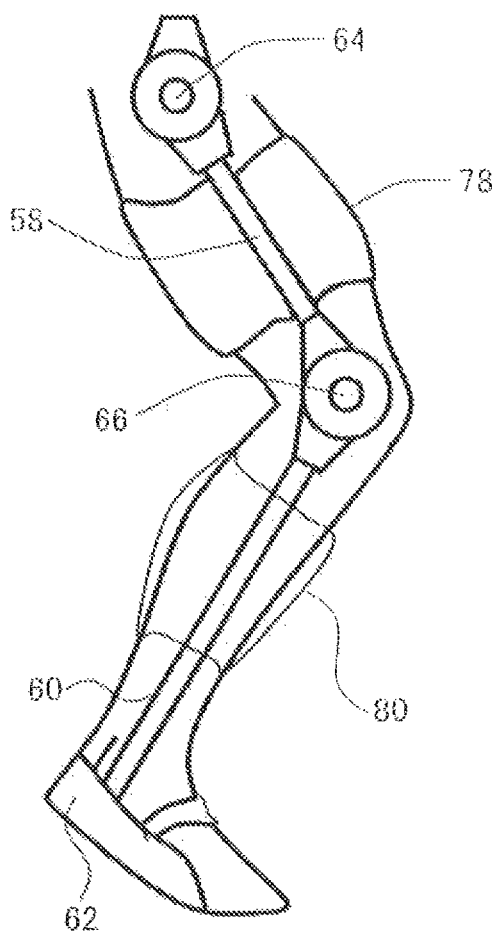
FIG. 7A is a diagram showing each element of a mathematical model, which is a side view of the leg of the wearer 12 who wears the action-assist wearing tool 18, when viewed from the side.
Figure 7B:
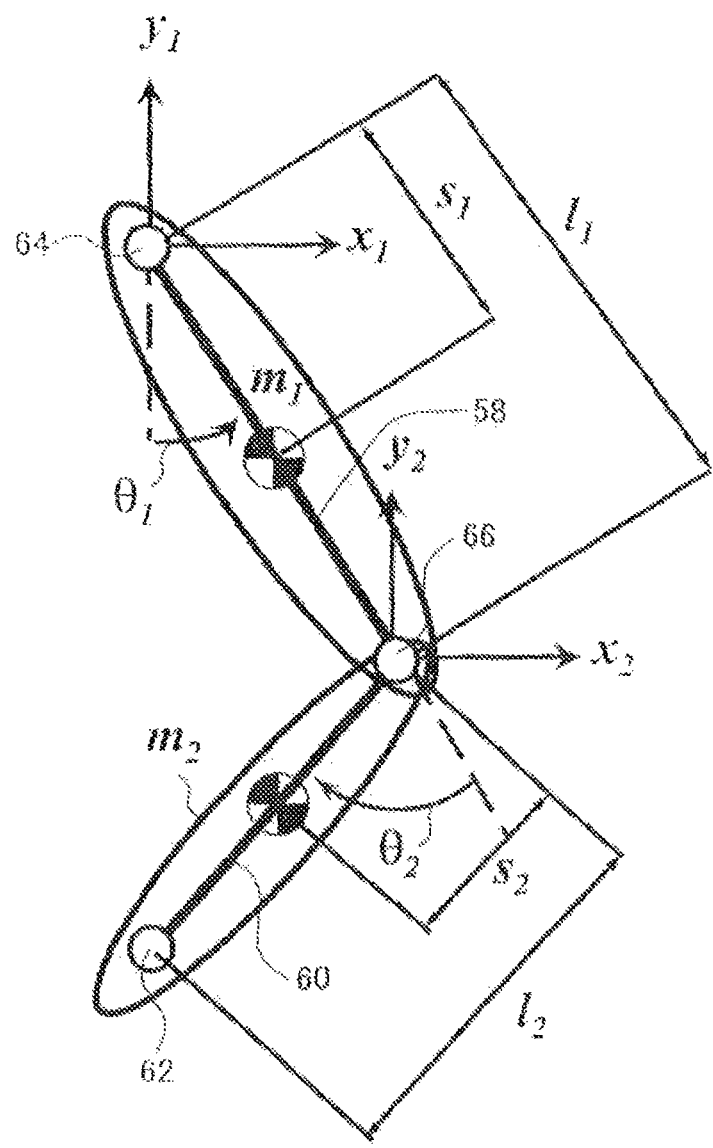
FIG. 7B is a diagram showing typically each element of a mathematical model which corresponds to the leg of the wearer 12.
Figure 8B:
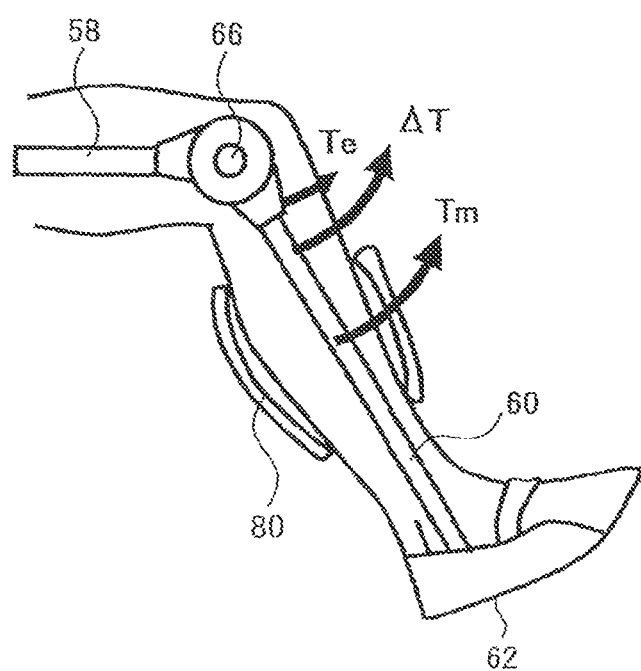
FIG. 8B is a diagram showing an action with the assisting force of the drive source 140 and the muscle force of the wearer 12, which shows typically each torque which acts when rotation the leg up (or front) around the knee joint.

FIG. 7A is a diagram showing each element of a mathematical model, which is a side view of the leg of the wearer 12 who wears the action-assist wearing tool 18 when viewed from the side. FIG. 7B is a diagram showing typically each element of a mathematical model which corresponds to the leg of the wearer 12. FIG. 8A is a diagram showing an action with the assisting force of the drive source 140 and the muscle force of the wearer 12, which shows that the resultant of the drive torque (Te) of the drive source 140 and the muscle torque (Tm) of the wearer 12 acts as a joint moment ($\Delta T$). FIG. 8B is a diagram showing an action with the assisting force of the drive source 140 and the muscle force of the wearer 12, which shows typically each torque which acts when rotating the leg up (or front) around the knee joint.

For example, when the wearer 12 rotates the leg up (or front) around the knee joint as shown in FIG. 8A and FIG. 8B, the third frame 60 of action-assist wearing tool 18 equivalent to the knee joint will be rotated around the second joint 66.

In that case, the wearer 12 well generate muscle force (Tm) as the torque acting on the knee joint, and the drive torque (Te) of the drive source 140 will act on the third frame 60 around the second joint 66.

Therefore, the resultant of the drive torque (Te) of the drive source 140 and the muscle torque (Tm) of the wearer 12 acts on the leg of the wearer 12 as the joint moment ($\Delta T$), and it is possible for the wearer 12 to operate the leg with a muscle force smaller than that in the case where the wearer does not wear the action-assist wearing tool 18.

And the drive torque of the drive source 140 (Te) is obtained according to the above-mentioned control system of the drive motors 20, 22, 24 and 26, and the joint moment ($\Delta T$) is determined based on the detection signal detected by the force sensors 45 and 46 (i.e., the detection signal of distortion produced by the difference between the drive torque (Te) and the muscle torque (Tm) of the wearer 12. However, the muscle torque (Tm) of the wearer 12 cannot be measured directly. To obviate the problem, in this embodiment, it is determined based on the difference between the joint moment ($\Delta T$) and the drive torque (Te).

$$R(q)\ddot{q}+D\dot{q}+Csgn(\dot{q}+G(q)+H(q,\dot{q})=T_e+T_m(u,q,\dot{q}) \quad (1)$$

In the above formula (1), the respective terms are represented as follows.

$$R(q) = \begin{bmatrix} J_\alpha + J_\beta + 2J_v\cos\theta & J_\beta + J_v\cos\theta \\ J_\beta + J_v\cos\theta & J_\beta \end{bmatrix}$$

$$J_\alpha = I_1 + m_1 s_1^2 + m_2 l_1^2$$
$$= (I_{e1} + I_{m1}) + (m_{e1} + m_{m1})s_1^2 + (m_{e2} + m_{m2})l_1^2$$

$$J_\beta = J_2 + m_2 s_2^2 = (I_{e2} + I_{m2}) + (m_{e2} + m_{m2})s_2^2$$

$$J_v = m_2 s_2 l_1 = (m_{e2} + m_{m2})s_2 l_1$$

$$G(q) = \begin{bmatrix} r_\alpha \sin\theta_1 + r_\beta \sin\theta_2 + r_v \sin(\theta_1 + \theta_2) \\ r_v \sin(\theta_1 + \theta_2) \end{bmatrix}$$

$$r_\alpha = m_1 g s_1 = (m_{e1} + m_{m1})g s_1$$

$$r_\beta = m_2 g l_1 = (m_{e2} + m_{m2})g l_1$$

$$r_v = m_2 g s_1 = (m_{e2} + m_{m2})g s_2$$

$$q = [\theta_1 \theta_2]^T$$

$$D = \begin{bmatrix} D_1 & 0 \\ 0 & D_2 \end{bmatrix} = \begin{bmatrix} D_{e1} & 0 \\ 0 & D_{e2} + D_{m2} \end{bmatrix}$$

$$C = \begin{bmatrix} C_1 & 0 \\ 0 & C_2 \end{bmatrix} = \begin{bmatrix} C_{e1} + C_{m1} & 0 \\ 0 & C_{e2} + C_{m2} \end{bmatrix}$$

$$H(q, \dot{q}) = \dot{R}(q)\dot{q} - \frac{1}{2}\frac{\partial}{\partial q}(\dot{q}^T R(q)\dot{q})$$

$$T_e = [\tau_{e1} \tau_{e2}]$$

$$T_m(u, q, \dot{q}) = [\tau_{m1}(u_1, \theta_1, \dot{\theta}_1)\tau_{m2}(u_2, \theta_2, \dot{\theta}_2]$$

$$u = [u_1 u_2]^T$$

In the above formula (1), subscript 1 means the parameter around a hip joint, subscript 2 means the parameter around a knee joint, subscript e means the parameter of the action-assist device 10, and subscript m means the parameter of the wearer 12.

Moreover, in the above formula (1), R(q) denotes the inertia term, G(g) denotes the gravity term, D denotes the viscous friction term, C denotes the Coulcomb friction term, H denotes the Coriolis force and centrifugal force term (which may be called also inertia term), Te denotes the drive torque by the drive source 140, Tm denotes the muscle moment term by the muscle force, and U denotes the degree-of-activity term by the muscle.

Next, the parameter identification method performed by the parameter identification unit 160 will be explained.

For the sake of simplicity, if it is assumed that the wearer 12 is in an inactive state, the muscle moment term Tm in the Formula (1) is negligible. And it may be expressed by the following formula (2) in this state.

$$R(q)\ddot{q}+D\dot{q}+Csgn(\dot{q})+G(q)+H(q,\dot{q})=T_e \quad (2)$$

The above formula (2) is transformed into the following formula (3) using the motion variable data matrix Ω and the kinetics parameter matrix X.

$$\Omega X = T_e$$

$$X = [J_\alpha J_\beta J_\gamma D_1 D_2 r_\alpha r_\beta r_\gamma C_1 C_2]^T \quad (3)$$

The motion variable data matrix Ω can be determined by various detection units and various estimation unit, whereas the kinetics parameter matrix X is unknown or varying because the parameters concerning the wearer 12 change depending on the individual difference or physical condition of the wearer 12.

Furthermore, the formula (3) can be transformed into the following formula (4) if the estimated kinetics parameter matrix X* for estimating the kinetics parameter matrix X is introduced using the error matrix ϵ which is equivalent to an error between the kinetics parameter matrix X and the estimated kinetics parameter matrix X*.

$$\Omega X^* = F_e + \epsilon \quad (4)$$

The unknown parameter (Pu) that minimizes the error matrix ϵ in the above formula (4) (to zero matrix) is represented by the following formula (5).

$$X^* = (\Omega^T \Omega)^{-1} (\Omega^T T_e) \quad (5)$$

Therefore, the unknown parameter (Pu) concerning the wearer 12 is derived by solving the above formula (5) (or by solving the equation of motion originally represented by the formula (1) as a result).

Next, the parameter identification processing and the torque estimation processing which are respectively performed by the parameter identification unit 160 and the joint torque estimation unit 152 when the above-mentioned action-assist wearing tool 18 is put on the wearer 12 will be explained.

Figure 9A:
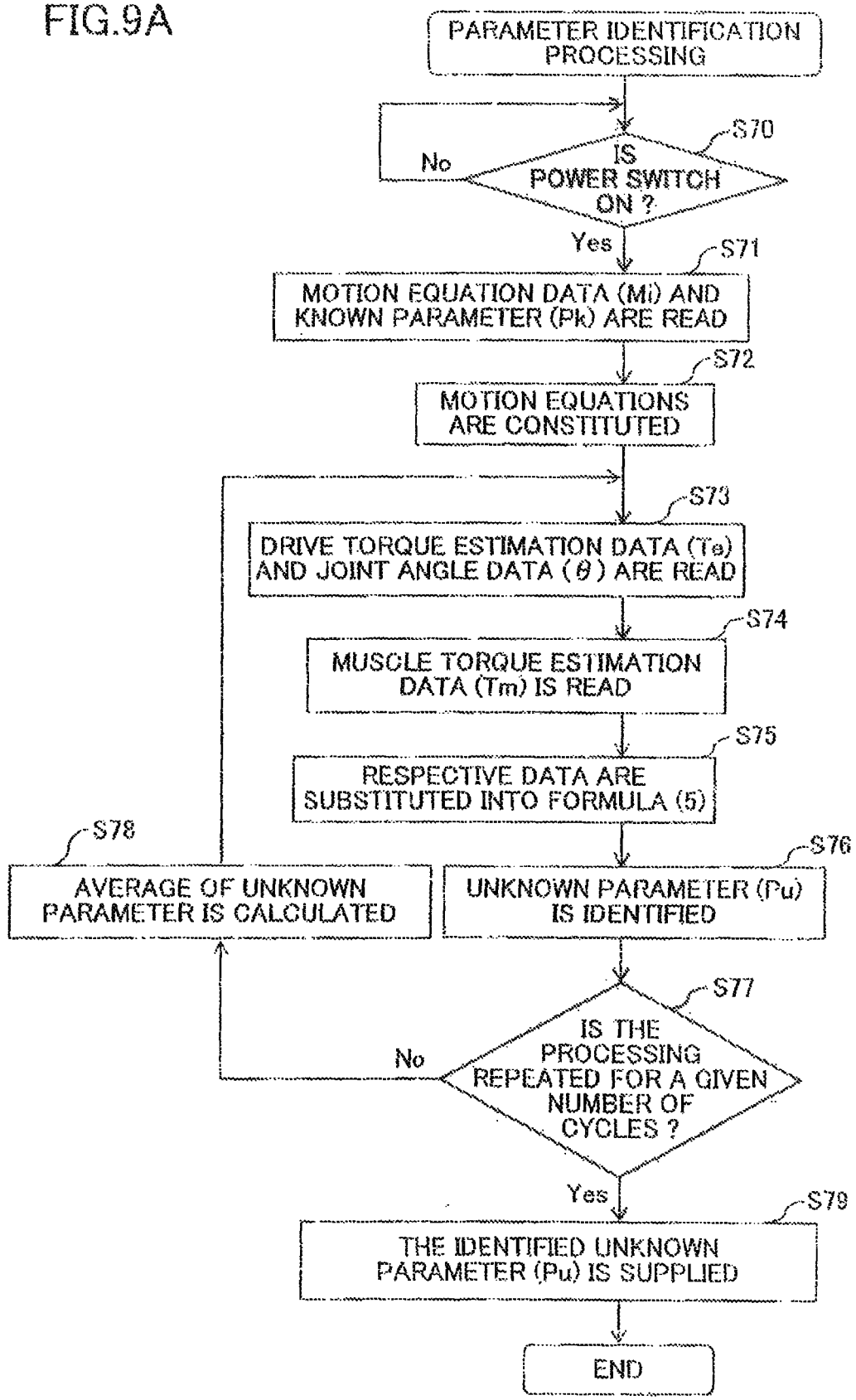
FIG. 9A is a diagram for explaining the parameter correction processing performed when the wearer 12 wears the action-assist wearing tool 18, which is a flowchart for explaining the procedure of parameter identification processing performed by a parameter identification unit 160.
Figure 9B:
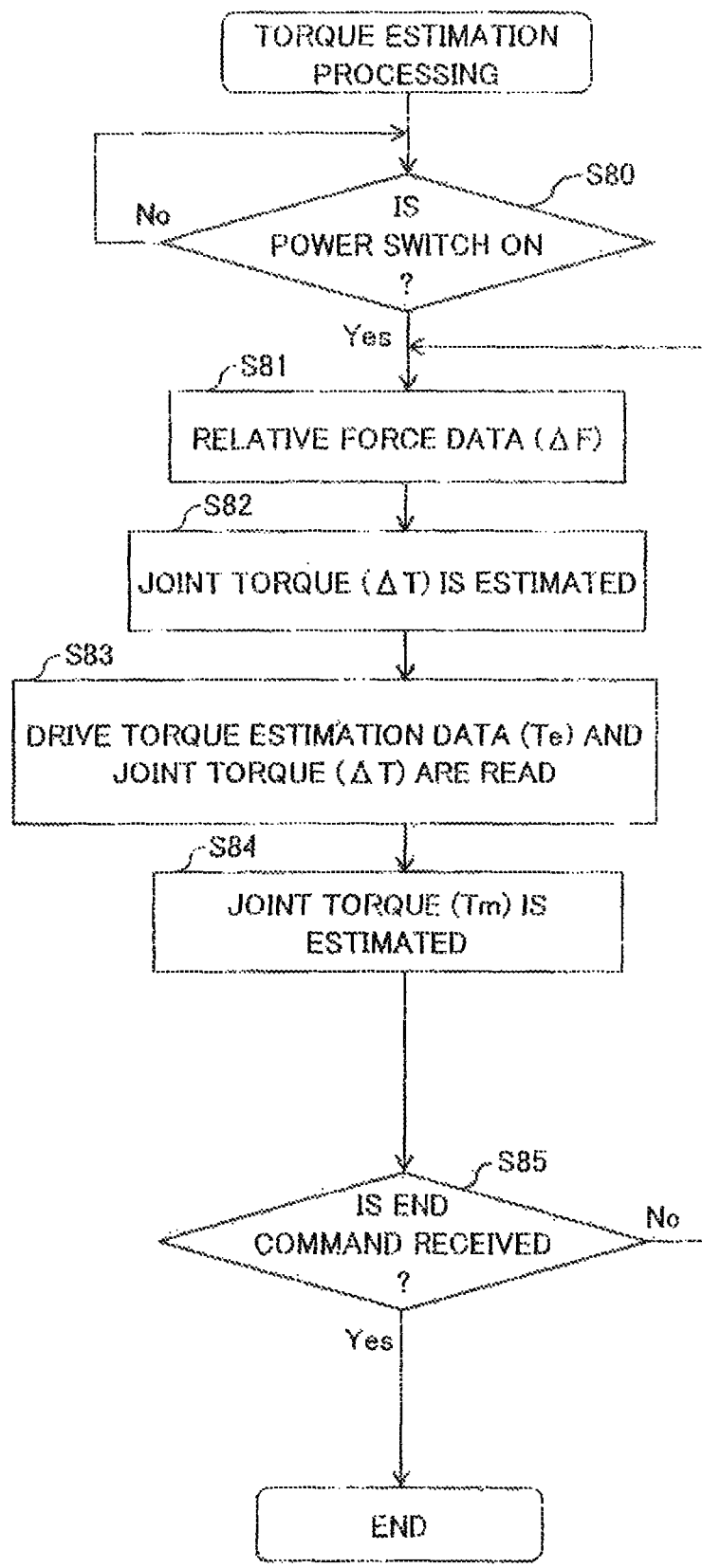
FIG. 9B is a diagram for explaining the parameter correction processing performed when the wearer 12 wears the action-assist wearing tool 18, which is a flowchart for explaining the procedure of torque estimation processing in which the joint torque is estimated by a joint torque estimation unit 152.

FIG. 9A is a diagram for explaining the parameter correction processing performed when the wearer 12 wears the action-assist wearing tool 18. This flowchart is for explaining the procedure of parameter identification processing performed by the parameter identification unit 160. FIG. 9B is a diagram for explaining the parameter correction processing performed when the wearer 12 wears the action-assist wearing tool 18. This flowchart is for explaining the procedure of torque estimation processing in which the joint torque is estimated by the joint torque estimation unit 152.

In the following, the parameter identification processing performed by the parameter identification unit 160 using the formulas mentioned above will be explained with reference to the flowchart of FIG. 9A. Also with reference to the flowchart of FIG. 9B, the relation with the processing performed by the joint torque estimation unit 152 will be explained collectively.

As shown in FIG. 9A, when the processing is started by the instructions from the control device 100, the parameter identification unit 160 determines whether the power switch (not shown) is turned ON (S70). If it is turned ON, the motion equation data (Mi) and the known parameter (Pk) are read from the data storing unit 156 (S71). Subsequently, the motion equation (the formulas (1)-(5)) are constituted on the operation environment of the CPU (S72).

In the meantime, as shown in FIG. 9B, the joint torque estimation unit 152 is operated when the power switch (not shown) is turned ON (S80). The relative force data (ΔF) detected by the relative force detection unit 146 is read (S81). After that, the joint moment (ΔT) is estimated by calculating a difference between the relative force data (ΔF) multiplied by the predetermined coefficient, and the drive torque estimation data (Te) (S82). Subsequently, the drive torque estimation data (Te) estimated by the drive torque estimation unit 150, and the joint moment estimation data (ΔT) estimated by the joint torque estimation unit 152 are read by the muscle torque estimation unit 153 (S83). And the muscle torque estimation unit 153 estimates a muscle torque (Tm) by the muscle force of the wearer 12 based on the association shown in FIG. 8A and FIG. 8B (S84). The joint torque estimation unit 152 and the muscle torque estimation unit 153 repeat performing the same processing before the end command from the control unit 200 is received (No in S85). And when the end command is received (Yes in S85), the processing is finished. In this embodiment, the muscle torque (Tm) is determined in order to allow the parameter identification even when the wearer 12 is in the situation where a muscle force is generated. This is the case where the parameter identification is performed in a stationary state.

Next, as shown in FIG. 9A, the drive torque estimation data (T') and the joint angle data (θ) are read from the data input unit 154 into the parameter identification unit 160 (S73), and the joint moment data (ΔT) is read from the joint torque estimation unit 152 into the parameter identification unit 160 (S74).

Subsequently, the parameter identification unit 160 substitutes the respective data into the formula (5) or the formula in which the muscle torque (Tm) is further considered suitably (S75), and identified the unknown parameters (Pu), such as the weight of each part of the wearer 12, the moment of inertia around each joint of the wearer 12, the coefficient of viscosity, and the Coulomb friction coefficient.

The series of processing steps from the reading of the drive torque estimation data (T'), the joint date (θ) and the joint moment data (ΔT) data, to the identification of the unknown parameters (Pu) is repeated for a predetermined number of cycles (for example, 10 cycles), and the average of the unknown parameters (Pu) is calculated for each cycle (S78).

Then, the parameter identification unit 160 supplies the thus identified unknown parameters (Pu) to the control unit 200 (S79). And the processing is terminated.

FIG. 10A, FIG. 10B, FIG. 10C, FIG. 11, FIG. 12A, and FIG. 12B show examples of experimental results in which the unknown parameters (Pu) of the wearer 12 are identified by the parameter identification unit 160.

In the identification experiment, suppose that the wearer 12 is in an inactive state, and the drive control of the drive source 140 is carried out by the control unit 200 according to the PD (proportional Derivative) control so that the joint angle θ of each joint may draw a predetermined locus. Moreover, suppose that the target angle of the joint angle θ follows the synthetic sinusoidal pattern including the frequencies of 0.2, 0.5 and 1.0 (Hz) so that the operation accuracy improves as much as possible within the range which fulfills the operating characteristic of the leg.

In consideration of the maximum bending angle in the action of the leg, the range of the joint angle θ (i.e., the operation range of the leg) falls within the range of −0.2 to 0.5 (rad) for the hip joint and within the range of 0 to 1.0 (rad) for the knee joint, respectively. The number of times of repetition for the averaging mentioned above is set to 10 times.

Figure 10A:
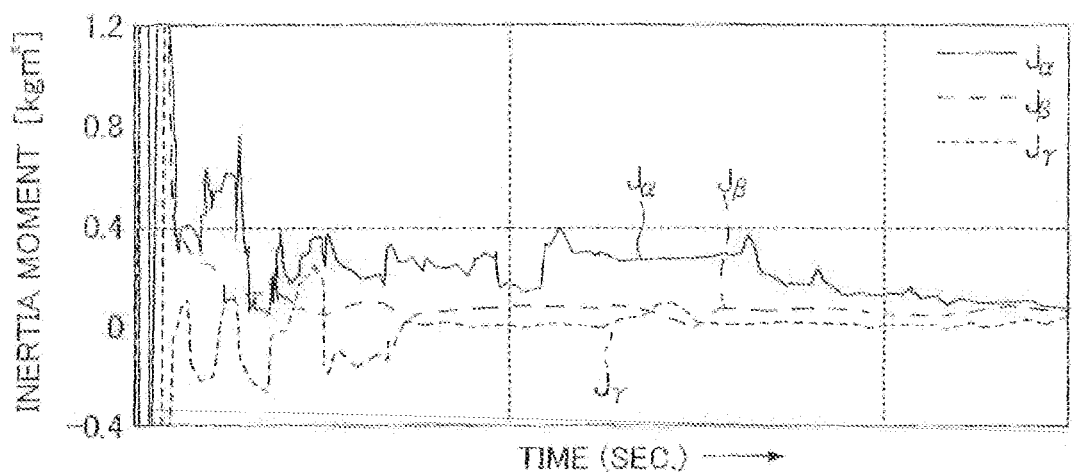
FIG. 10A is a diagram showing experimental data of the transient response of the kinetics parameters containing the unknown parameter (Pu) at the time of performing parameter identification processing, which shows the convergence pattern of moment of inertia.
Figure 10B:
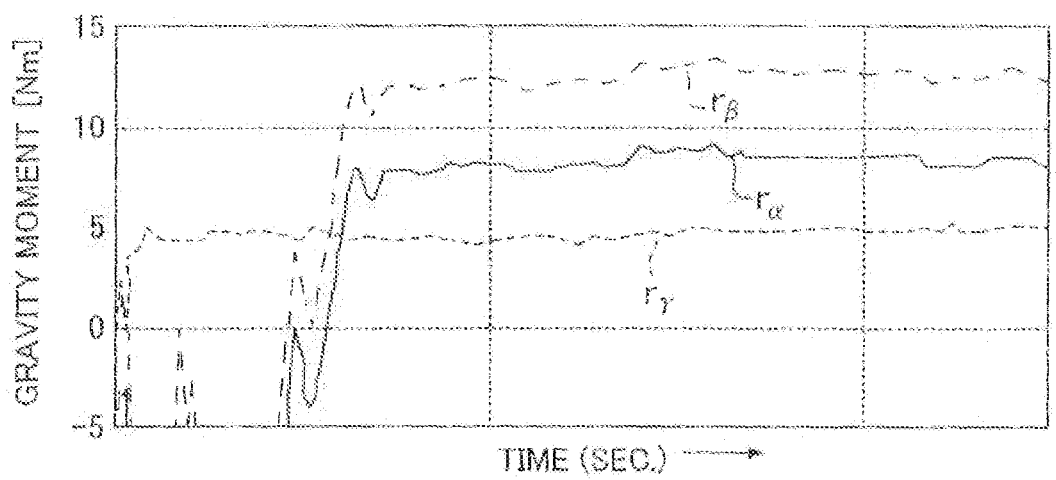
FIG. 10B is a diagram showing experimental data of the transient response of the kinetics parameters containing the unknown parameter (Pu) at the time of performing parameter identification processing, which shown the convergence pattern of a gravity moment.

FIG. 10A shows the experimental data of the transient response of the kinetics parameters containing the unknown parameters at the time of performing the parameter identification processing (Pu). This graph shown the convergence pattern of the inertia moment. FIG. 10B is a graph which shows the convergence pattern of the gravity moment, and FIG. 10C is a graph which shows the convergence pattern of the coefficient of viscous friction.

Figure 10C:
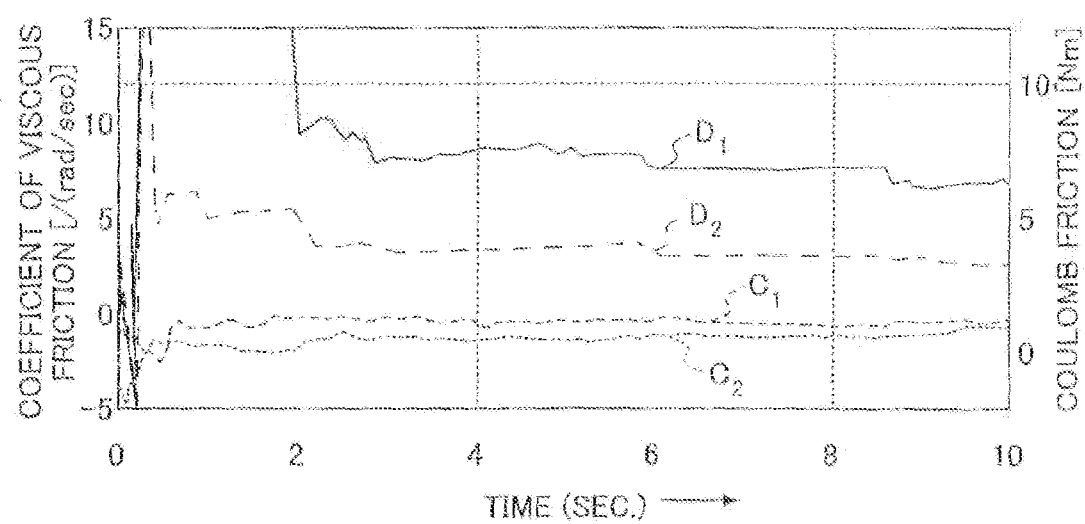
FIG. 10C is a diagram showing experimental data of the transient response of the kinetics parameters containing the unknown parameter (Pu) at the time of performing parameter identification processing, which shown the convergence pattern of the coefficient of viscosity.

As is apparent from FIG. 10A, FIG. 10B and FIG. 10C, it is turned out that, according to the above-mentioned parameter identification processing by the parameter identification unit 160 of this embodiment, most of the kinetics parameters of the wearer 12 are made convergent within several seconds and it has excellent convergence. In other words, the identification processing can be performed for a short time.

FIG. 11 shows the experimental data in which the experimental results when the parameter identification processing under the same conditions is performed for each of the tested persons A, B and C as the wearer 12 are shown. It is shown that the individual differences accompanied with the physical differences of the tested persons A, B and C are included in the kinetics parameters, such as the moment of inertia, the viscous friction coefficient, the gravity moment and the Coulomb friction.

Namely, since the tested persons A, B, and C differ in the physical features, such as the height and the weight, respectively, the step distance and the muscle force of each person also differ when each person performs walk operation. As is apparent from the experimental data of FIG. 11, the moment of inertia, the viscous friction coefficient, the gravity moment and the Coulomb friction are different for the individual tested persons even when the parameter identification processing is performed under the same conditions.

Therefore, when the wearer 12 wears the action-assist wearing tool 18, it is possible to correct the kinetics parameters of the wearer who has different physical features by performing the above-mentioned parameter identification processing, so that the assisting force in conformity with that wearer may be acquired.

Figure 12A:
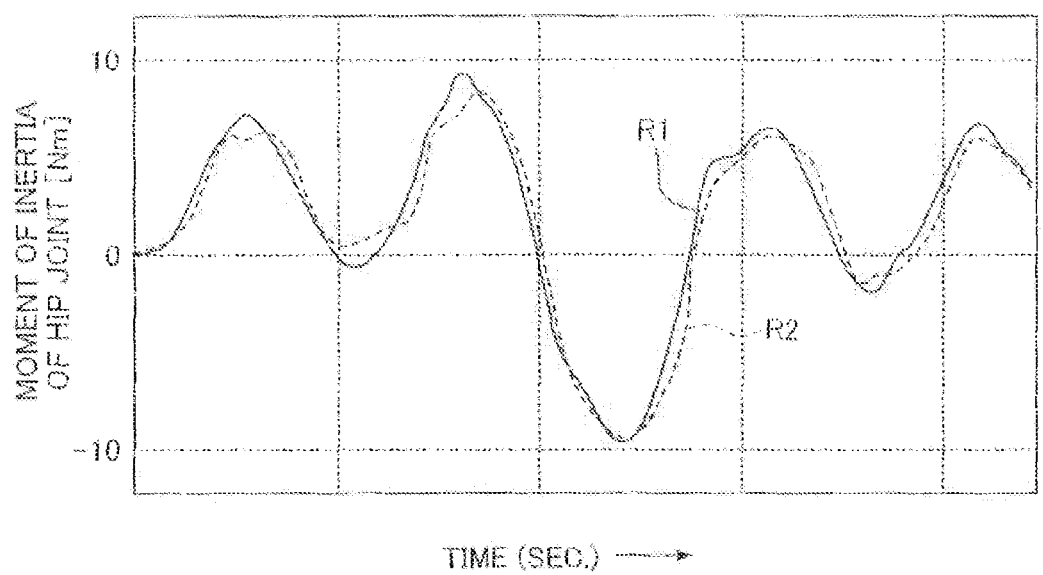
FIG. 12A is a diagram showing experimental data of a example of the identification accuracy by the parameter identification processing of this embodiment, which shows the identification accuracy of the moment of inertia of the hip joint accompanied with the walk operation.
Figure 12B:
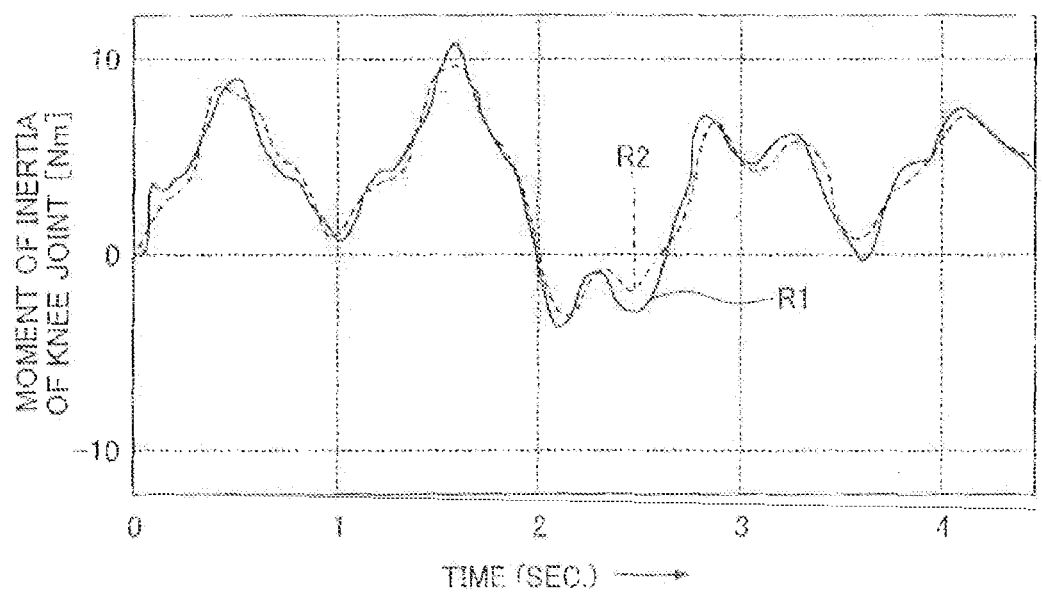
FIG. 12B is a diagram showing experimental data of an example of the identification accuracy by the parameter identification processing of this embodiment, which shows the identification accuracy of the moment of inertia of the knee joint accompanied with the walk operation.

FIG. 12A shows the experimental data of an example of the identification accuracy by the parameter identification processing of this embodiment, which shows the identification accuracy of the moment of inertia of the hip joint accompanied with the walk operation. FIG. 12B shows the identification accuracy of the moment of inertia of the knee joint accompanied with the walk operation.

In the graphs shown in FIG. 12A and FIG. 12B, the graph of the actually measured values (R1) and the graph of the identified values (R2) are overlapped to each other with respect to the transient response of the moment of inertia about each of the hip joint and the knee joint, and it is turned out that the graph of the actually measured values and the graph of the identified values are mostly in agreement with each other. Namely, the actually measured values (R1) and the identified values (R2) in FIG. 12A and FIG. 12B resemble closely mutually, proving that sufficient identification accuracy can be obtained.

Figure 13:
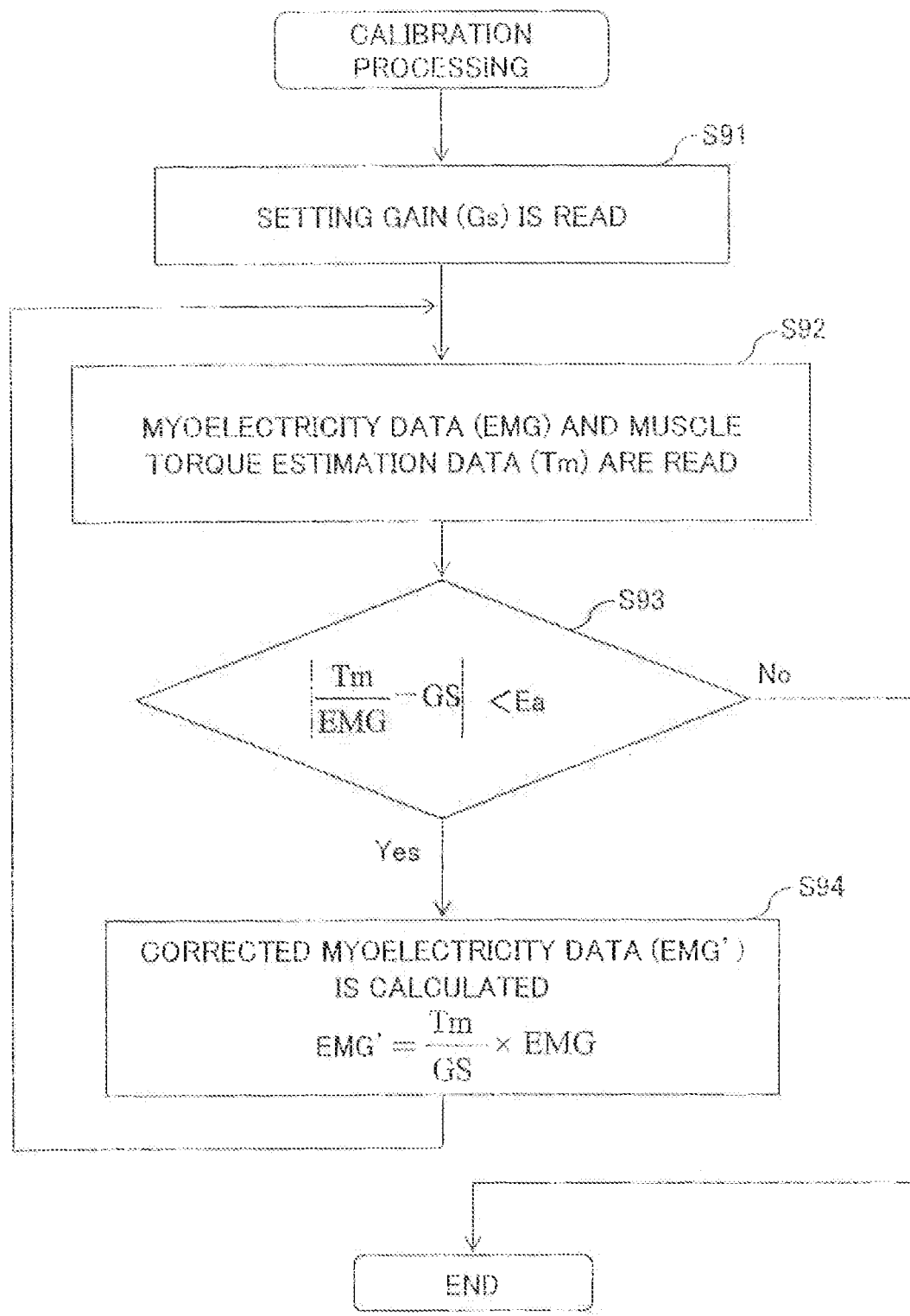
FIG. 13 is a flowchart for explaining the procedure of calibration processing which is performed by a calibration unit 158.

FIG. 13 is a flowchart for explaining the procedure of calibration processing which is performed by the calibration unit 158. In the following, the parameter identification processing using the calibration unit 158 will be explained with reference to FIG. 13.

Upon start, the calibration unit 158 reads the setting gain (Gs) from the data storing unit 156 (S91), and subsequently, reads the myoelectricity data (EMG) and the muscle torque estimation data (Tm) from the data input unit 160 (S92).

Next, the calibration unit 158 determined whether a difference between a ratio (Tm/EMG) of the muscle torque estimation data (Tm) and the myoelectricity data (EMG) and the setting gain (Ga) is larger than a permissible error range (Ea) (S93).

When the difference (Tm/EMG)-(Gs) is larger than the error range (Ea) (Yes in S93), the calibration unit 158 corrects the myoelectricity data (EMG) based on the following formula (6) and calculated the corrected myoelectricity data (EMG'). And the processing control is returned to the step of reading the myoelectricity data (EMG) and the muscle torque estimation data (Tm) from the data input unit 160.

On the other hand, when it is determined that the difference (Tm/EMG)-(Gs) is less than the error range (Ea) (NO in S93), the calibration unit 158 terminates the processing.

$$EMG'=(T_m/G_s) \times EMG \qquad (6)$$

According to the above calibration processing, the ratio (Tm/EMG') of the muscle torque estimation data (Tm) and the corrected source potential data (EMG') is almost equal to the setting gain (Gs). It is possible to prevent beforehand the situation in which a poor sensitivity and oversensitivity arises in the detection result from the biosignal detection unit 144.

As a result, it is possible to prevent the situation where the identification accuracy of the unknown parameters (Pu) of the wearer 12 mentioned above falls, and it is possible to also prevent the situation where the assisting force generated by the drive source 140 becomes too small or too large.

In the action-assist device 10 of this embodiment, the muscle torque (Tm) or muscle force of the wearer 12 can be obtained by the joint torque estimation unit 152 and the muscle torque estimation unit 153, and a calibration is performed using the obtained muscle torque. It is possible to reduce remarkably the burden on the wearer 12 when compared with that in the case of the device without these units. Specifically, if neither the joint torque estimation unit 152 nor the muscle torque estimation unit 153 is used, it is necessary to force the wearer 12 to maintain the stationary state over a predetermined time while a predetermined drive torque (Te) is given by the drive source 140 in this state, in order to obtain the muscle torque (Tm) or muscle force of the wearer 12. This will cause the wearer 12 to create the needed muscle force, regardless of the muscle force that can be produced by the wearer 12, and will also force the wearer 12 to wait for the necessary latency time. According to the action-assist device 10 of this embodiment, the burden on the wearer can be reduced desirably.

Next, the control method applied to the control device 100 will be explained.

The control method applied to the action-assist device 10 is not limited. For example, a control method based on the classical control theory, such as the PD control, may be applicable, similar to the parameter identification experiment. Accordingly to the action-assist device 10 of this embodiment, even if the classical control theory is based, the controlled system including the wearer 12 is identified, and thereafter the simulation in which the identification result is incorporated can be performed and the parameters of the optimal compensator can be set up on the simulation concerned. And it is possible to demonstrate sufficient effect according to the control method. Specifically, it is possible to give the assisting force which the wearer 12 optionally as a result of demonstrating the effect according to the control method by carrying out feedback control of the myoelectricity (EMG) from the biosignal detection unit 144, even if it is based on the classical control theory.

The control method applied to the control device 100 may not be based on the modern control theory which uses an optimal regulator, the optimal observer, etc., and is not limited in particular.

(Control Method Which Performs Gravity Compensation)

This control method performs compensation of the gravity term G (q) in the formula (1) mentioned above and suppresses the influence of the gravity term G (q) concerned.

The PD control is adopted as a control method used as a base supposing operating so that the action-assist device 10 with which the wearer 12 was equipped may be set to the target posture θe from the initial posture θs as a precondition.

First, if it is the usual PD control, the PD feedback control input (control signal Ur) concerning the drive torque (Te) by the drive source 140 is represented by the following formula (7).

$$R(q)\ddot{q}+D\dot{q}+Csgn(\dot{q})+G(q)+H(q,\dot{q})=T_e+T_m(u,q,\dot{q})$$

$$Ur=-K_p(\theta_s-\theta_e)-K_D\dot{q} \quad (7)$$

Next, in the PD control which performs gravity compensation as well, the PD feedback control input (control signal Ur) concerning the drive torque (Te) by the drive source 140 is represented by the following formula (8).

$$R(q)\ddot{q}+D\dot{q}+Csgn(\dot{q})+G(q)+H(q,\dot{q})=T_e+T_m(u,q,\dot{q})$$

$$Ur=-K_p(\theta_s-\theta_s)-K_D\dot{q}+G(q) \quad (8)$$

In the PD control with the gravity compensation expressed by the formula (8), when feedback control is carried out, the gravity term G(q) can be cancelled, and the weight of the wearer 12 himself and the weight of the action-assist wearing tool 18 acting on the wearer 12 when wearing the action-assist wearing tool 18 can be reduced.

(Control Method which Performs Inertia Compensation)

This control method performs compensation of the inertia term R (q) in the formula (1) mentioned above, and suppressed the influence of the inertia term R (q) concerned.

The PD control is adopted as a control method used as a base supposing operation so that the action-assist device 10 with which the wearer 12 was equipped may be set to the target posture θe from the initial posture θ s as a precondition similar to the case of gravity compensation.

In the PD control which performs inertia comensation as well, the PD feedback control input (control signal Ur) concerning the drive torque (Te) by the drive source 140 is represented by the formula (9).

$$R(q)\ddot{q}+D\dot{q}+Csgn(\dot{q})+G(q)+H(q,\dot{q})=T_e+T_m(u,q,\dot{q})$$

$$Ur=-K_p(\theta_s-\theta_e)-K_D\dot{q}+H(q,\dot{q}) \quad (9)$$

In the PD control with the inertia compensation according to the formula (9), it is possible that, when feedback control is carried out to offset the inertia term H of the controlled system, and the force of inertia by the wearer 12 by himself and the force of inertia from the action-assist wearing tool 18 can be suppressed, and especially when trying to perform quick operation, the burden on the wearer 12 can be reduced remarkably.

(Control Method which Performs Gravity Compensation and Inertia Compensation)

This control method utilizes advantageous features picked up from both the above PD control with the gravity compensation and the above PD control with the inertia compensation. And it is represented by the formula (10) under the same condition as that of the previously mentioned formula.

The operation and effect of this control method are the same as those of the PD control with the gravity compensation and the PD control with the inertia compensation described above, and a description thereof will be omitted.

$$R(q)\ddot{q}+D\dot{q}+Csgn(\dot{q})+G(q)+H(q,\dot{q})=T_e+T_m(u,q,\dot{q})$$

$$Ur=-K_p(\theta_s-\theta_e)-K_D\dot{q}+G(q)+H(q,\dot{q}) \quad (10)$$

Impedance Control)

The impedance control is to freely adjust the characteristics, such as the inertia, the viscosity and the rigidity of the controlled system, taking into consideration of the viscoelasticity characteristic of the human being (the wearer 12). And it has the feature that the force acting between the controlled system and the environment can be appropriately chosen according to the purpose of control. In the action-assist device 10, the characteristic of the entire system including the wearer 12 and the action-assist device 10 is changed, thereby it is possible to change the characteristic of the wearer 12 indirectly and to perform the control.

Namely, when the impedance control is applied to control device 100, by using the action-assist device 10 which is put on the wearer 12, it is possible to realize adjusting the characteristic (impedance) of the wearer 12 indirectly, which could not be accomplished by the conventional device.

The controlled system by the impedance control applied to the control device 100 is the entire system including the action-assist device 10 and the wearer 12. Since it is quite different from the usual impedance control, it will be called hybrid impedance control, in order to distinguish this impedance control from the usual impedance control.

For example, if the control is performed so that the drive torque generated by the drive source 140 is represented by Te' of the following formula (11), the formula (1) is transformed into the following formula (12).

Consequently, as apparent the formula (12), the inertia term R(q) for the entire system is changed to [R(q)-R'(q)], and the viscous friction term D is changed to (d-D'). As for these terms, the adjustment can be performed by setting up R'(q) and D' suitably.

In this case, since the influence of the inertia term or the viscous friction term from the action assist device 10 can be suppressed, it is possible to demonstrate the original capability of the wearer 12 to perform quick action, such as reflection, to the maximum extent.

The influence of the inertia term or the viscous friction term of the wearer 12 can also be suppressed, and the wearer 12 is permitted to walk earlier than the original cycle, or to operate more smoothly (smaller viscous friction) than in the case where the action-assist wearing tool is not put on.

$$T'_e=-R'(q)\ddot{q}-D'\dot{q}+T_e \quad (11)$$

$$[R(q)-R'(q)]\ddot{q}+(D-D')\dot{q}+Csgn(\dot{q})+G(q)+H(q,\dot{q})=T_eT_m(u,q,\dot{q}) \quad (12)$$

In the above-described control device 100, the control mechanism can be constituted with at least one of the gravity compensation, the inertia compensation, and the hybrid impedance control applied. Specifically, the control method data (Ci) of one of these control methods is read into the control unit 200 from the data storing unit 156, and the control mechanism can be constituted on the operation environment of the control unit 200 based on the control method data (Ci) concerned.

According to the thus constituted control mechanism, it is possible to generate the control signal Ur according to the predetermined control method based on the acquired respective detection data and estimated data, and, as a result, the assisting force in conformity with the control method concerned can be given to the wearer 12.

FIGS. 14A, 14C, FIGS. 15A-15C and FIGS. 16A-16C show the effect when the hybrid impedance control is applied to the control device 100, and show the experimental results when the wearer 12 is made to perform the same operation.

Figure 14A:
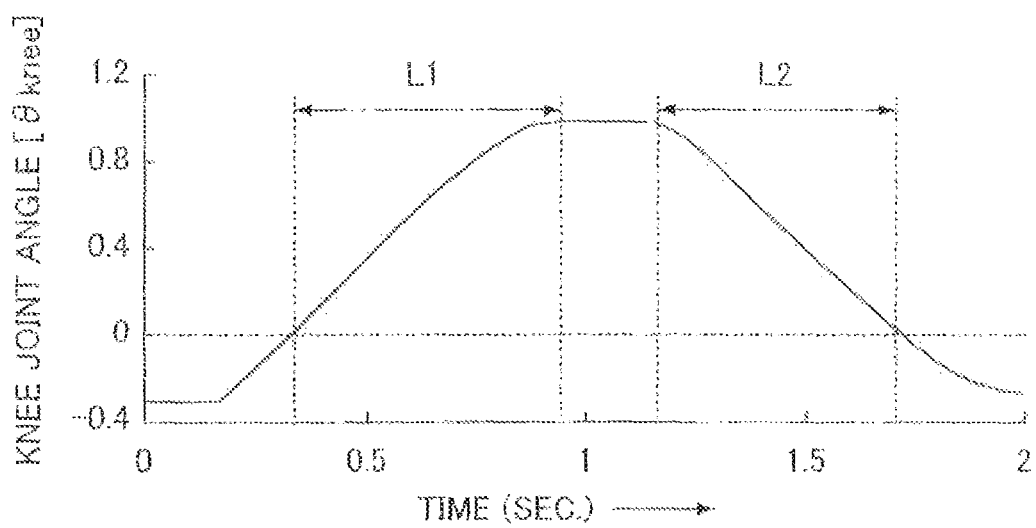
FIG. 14A is a diagram showing a knee joint angle change without control (without an assisting force).
Figure 14B:
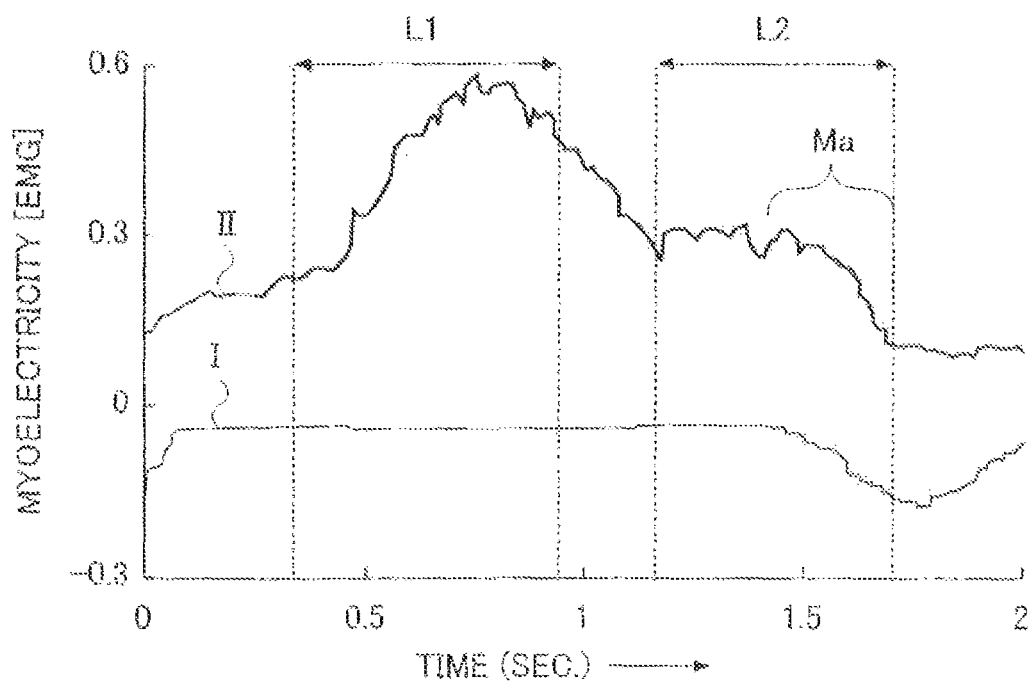
FIG. 14B is a diagram showing a myoelectricity change without control (without an assisting force).
Figure 14C:
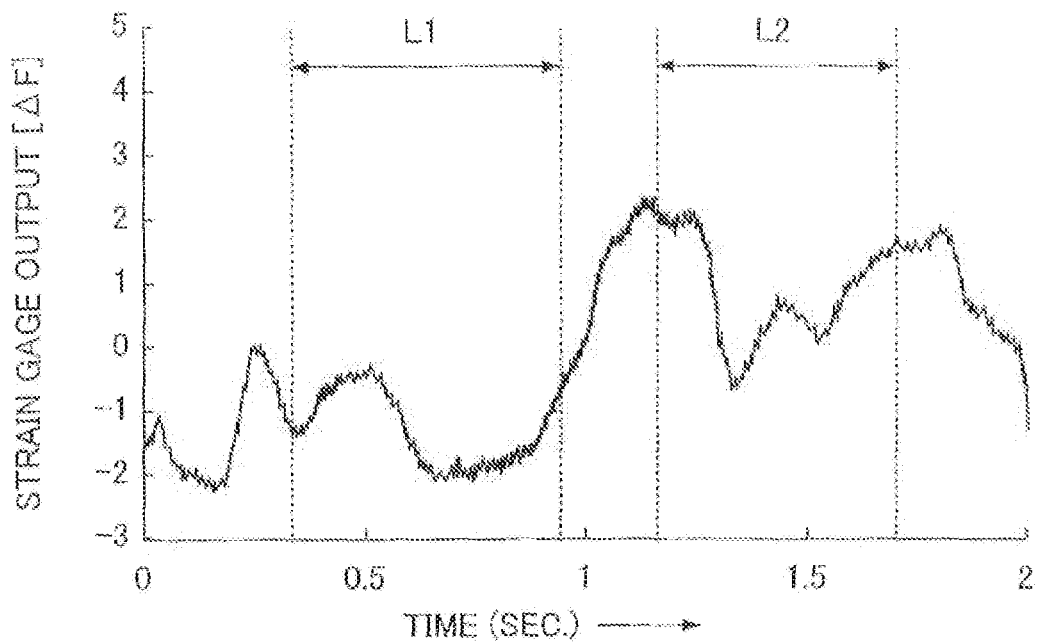
FIG. 14C is a diagram showing a strain gage output change without control (without an assisting force).

Specifically, FIG. 14A is a diagram showing a knee joint angle change without control (without an assisting force). FIG. 14B is a diagram showing a myoelectricity change without control (without an assisting force). FIG. 14C is a diagram showing a strain gage output change without control (without an assisting force).

Figure 15A:
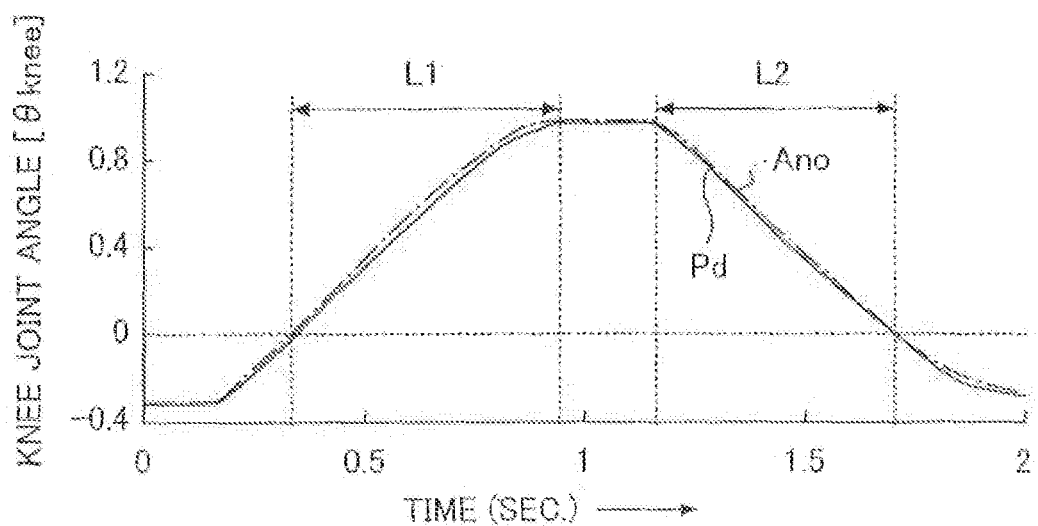
FIG. 15A is a diagram showing a knee joint angle change with the assisting force by the PD control.
Figure 15B:
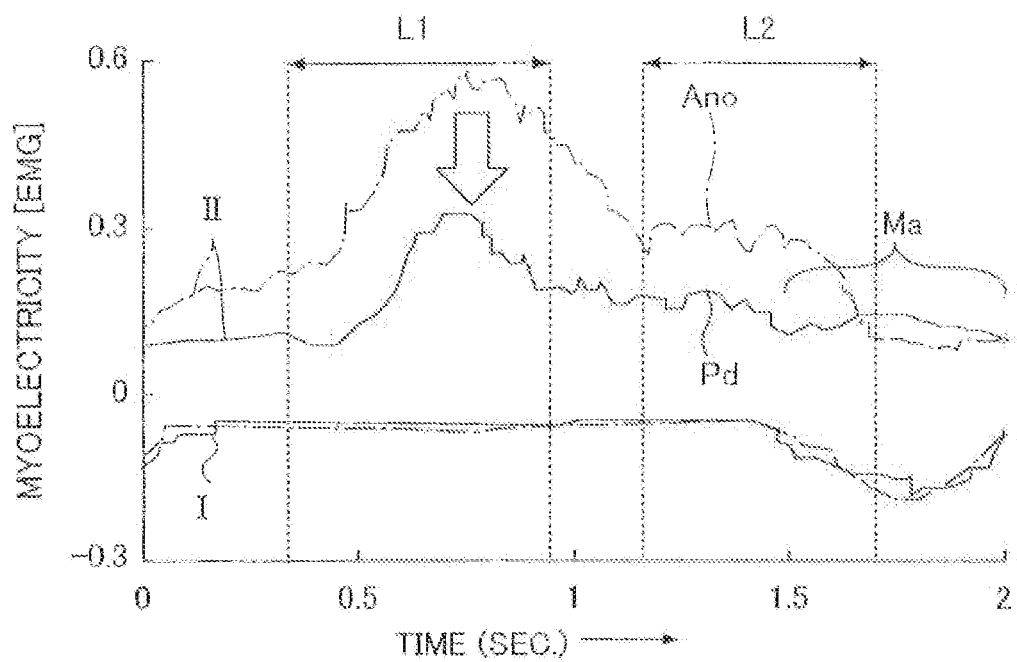
FIG. 15B is a diagram showing a myoelectricity change with the assisting force by the PD control.
Figure 15C:
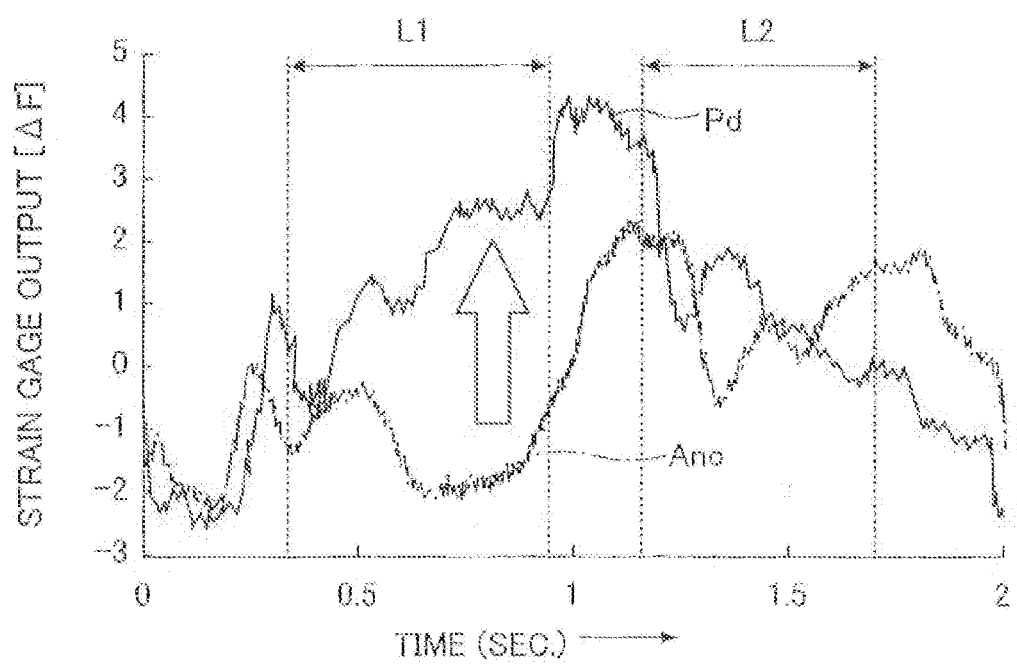
FIG. 15C is a diagram showing a strain gage output change with the assisting force by the PD control.

FIG. 15A is a diagram showing a knee joint angle change with the assisting force by the PD control. FIG. 15B is a diagram showing a myoelectricity change with the assisting force by the PD control. FIG. 15C is a diagram showing a strain gage output change with the assisting force by the PD control.

Figure 16A:
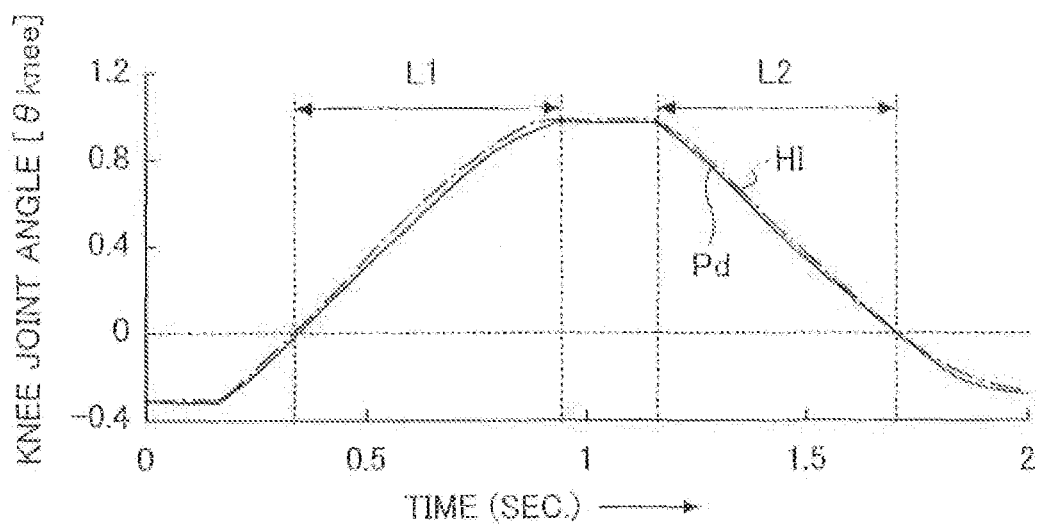
FIG. 16A is a diagram showing a knee joint angle change with the assisting force by the PD control+hybrid impedance control.
Figure 16B:
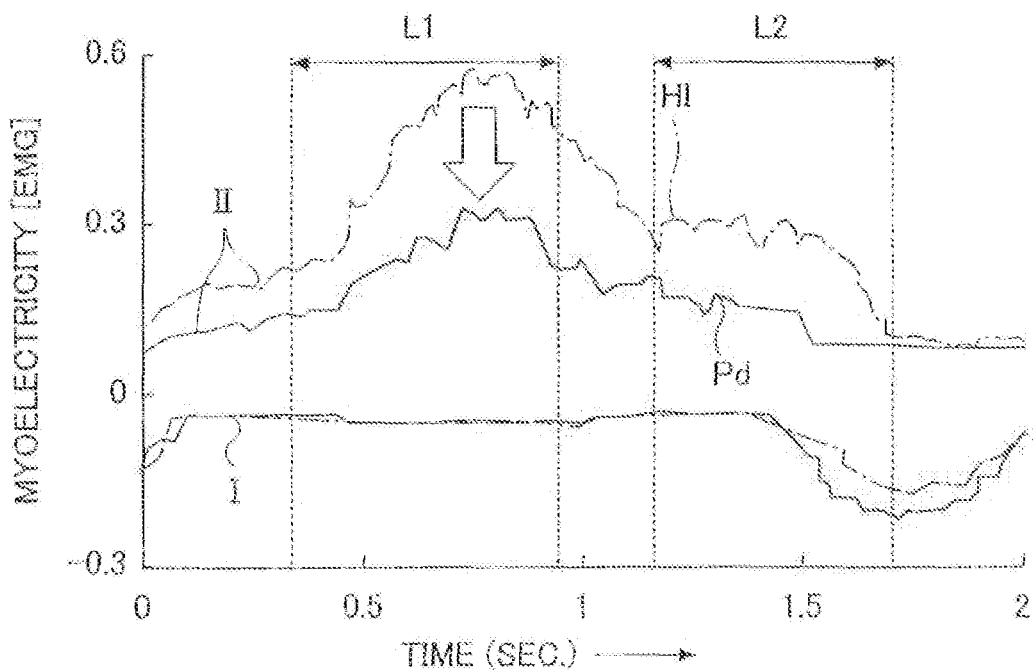
FIG. 16B is a diagram showing a myoelectricity change with the assisting force by the PD control+hybrid impedance control.
Figure 16C:
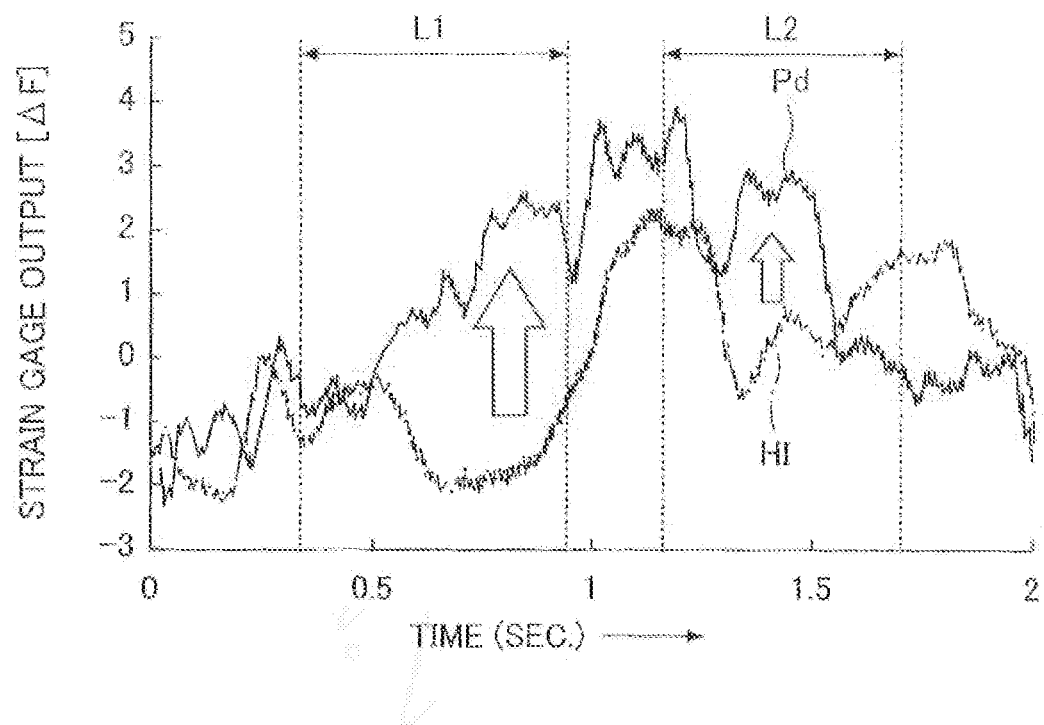
FIG. 16C is a diagram showing a strain gage output change with the assisting force by the PD control+hybrid impedance control.

FIG. 16A is a diagram showing a knee joint angle change with the assisting force by the PD control+ hybrid impedance control. FIG. 16B is a diagram showing a myoelectricity change with the assisting force by the PD control+ hybrid impedance control. FIG. 16C is a diagram showing a strain gage output change with the assisting force by the PD control+ hybrid impedance control.

The experimental condition is as follows. When a series of actions to swing up the leg forward in the sitting state and thereafter swing down the leg is performed by the wearer 12, the myoelectricity (EMG) and the relative force for the force sensor output which is converted into the relative force) from the wearer 12 who performs each action concerned are measured.

In FIG. 14A, FIG. 14B, and FIG. 14C, it is shown that the myoelectricity (EMG) from the wearer 12 is relatively large during a swing-up period (L1), and during a swing-down period (L2), the myoelectricity (EMG) becomes small relatively. This is in conformity with the experience.

However, it is confirmed that there is the portion in the second half of the swing-down period (L2), where reduction of the myoelectricity (EMG) of the shrunk muscle (graph II) from the expanded muscle (graph I) is barred. This phenomenon arise because interaction force moment Ma acts on the wearer 12 according to the inertia of the action-assist wearing tool 18.

In the graph shown in FIG. 14C, the strain gage output of the force sensor 46 is changing although the assisting force is not supplied. This is because, when the wearer 12 changes the angle of the knee joint, the load of the second joint 66 (or the load of the drive motors 24 and 26 and the motor drive force transfer system) is acting on the third frame 60.

In contrast, from FIG. 15A, FIG. 15B and FIG. 15C, showing the experimental result when the PD control is performed (Pd: indicated by the solid line), it is turned out that the myoelectricity (EMG) from the wearer 12 is generally halved when compared with the case when no assisting force is supplied (Ano: indicated by the one-dot chain line), the response waveform during the swing-up period (L1) resembles closely, and a suitable action-assist control is performed. This is also supported by the fact that the force sensor output (the relative force ΔF) during the swing-up period (L1) is increased from that in the case (Ano) where no assisting force is supplied.

However, in FIG. 15A, FIG. 15B, and FIG. 15C, in the second half of the swing-down period (L2), the influence of the above interaction force moment Ma appears, and although the magnitude itself is relatively small, it may supply the wearer 12 with sense of incongruity.

In contrast, from FIG. 16A, FIG. 16B and FIG. 16C, showing the experimental result when the PD control+ hybrid impedance control (HI: indicated by the one-dot chain line) is performed, it is turned out that the influence of the interaction force moment which is the problem when only the PD control is performed can be suppressed in this case, in addition to the above-mentioned effect of the PD control (Pd: indicated by the solid line).

Namely, it is turned out that according to the PD control+ hybrid impedance control (HI), the myoelectricity (EMG) of the wearer 12 not only during the swing-up period (L1) but also during the swing-down period (L2) is halved, the response waveform resembles closely, and a suitable action-assist control is performed over the whole period.

As explained above, according to the action-assist device 10 of this embodiment, the parameter identification unit 160 identifies the kinetics parameters intrinsic to the wearer 12 concerned in the state where the wearer 12 puts on the action-assist wearing tool 18, and the drive source 140 can be controlled by the control device 100 based on the equation of motion (the formula (5) etc.) into which the identified kinetics parameters are substituted. It is possible to demonstrate sufficient effect in conformity with the control method used by the control device 100 without being influenced by the change factors, such as the wearer's individual difference and physical condition.

In the action-assist device 10 of this embodiment, the estimated muscle torque (Tm) from the muscle torque estimation unit 153 is also substituted into the equation of motion (the formula (1) etc.), and the drive source 140 can be controlled by the control device 100 based on the equation of motion into which the estimated muscle torque (Tm) is substituted. Also in the state where a muscle force is produced by the wearer 12, the kinetics parameters can be identified, and the above-mentioned effect can be demonstrated, without causing the wearer 12 to wait for the latency time for identifying the kinetics parameters concerned.

The action-assist device 10 of this embodiment may be configured to include the calibration unit 158 which adjusts a gain between the myoelectricity (EMG) detected by the biosignal detection unit 144 and the muscle torque (Tm) detected by the muscle torque estimation unit 153 so that the association between the myoelectricity (EMG) and the muscle torque (Tm) is in conformity with the predetermined setting gain (Gs). It is possible to prevent beforehand the situation in which a poor sensitivity and oversensitivity arises from the detection result from the biosignal detection unit 144.

As a result, it is possible to avoid the situation where the identification accuracy of the kinematics parameters of the wearer 12 falls, and it is possible to avoid the situation where the assisting force generated by the drive source 140 becomes too small or too large. Moreover, in the action-assist device 10 of this embodiment, a calibration can be performed also in the state where the muscle force is produced by the wearer 12, and the wearer 12 is not forced to wait for the latency time of the calibration concerned.

In the action-assist device 10 of this embodiment, the control device 100 may be configured to control the drive source according to a control method using the kinetics parameter identified by the parameter identification unit 160, and performing at least one of gravity compensation and inertia compensation. It is possible to suppress the situation where the weight of the action-assist device 10 may give the wearer a sense of burden, and the situation where the inertia of the action-assist device 10 may give the wearer 12 a sense of incongruity at the time of operation.

In the action-assist device 10 of this embodiment, the control device 100 may be configured to control the drive source according to the hybrid impedance control method using the kinetics parameters identified by the parameter identification unit 160. It is possible to demonstrate sufficient effect in conformity with the hybrid impedance control method in which the apparent inertia, the apparent viscosity, etc. of the action-assist device 10 are reduced so as to realize light operation.

INDUSTRIAL APPLICABILITY

In the above-mentioned embodiment, the composition of the action-assist device 10 in which an assisting force is given to the leg of the wearer 12 has been described. This invention is not limited to the above example. It is a matter of course that this invention is also applicable to an action-assist device in which an assisting force is given to the arm of the wearer, for example.

In the above-mentioned embodiment, the composition in which a drive torque of an electric motor is transmitted as assisting force has been described. It is a matter of course that this invention is also applicable to an action-assist device in which an assisting force is generated using another drive source other than an electric motor.

This international application is based upon and claims the benefit of priority of Japanese patent: application No. 2005-18295, filed on Jan. 26, 2005, the contents of which is hereby incorporated by reference.

The invention claimed is:

1. A method of providing rehabilitation training to a wearing person experiencing compromised functionality in moving a limb around a joint, the method comprising:
   using a wearable action-assisting device which is controlled based on a myoelectricity signal from the wearing person when the person moves the limb around the joint; and
   in the course of using the wearable action-assisting device, having the wearing person perform a series of physical tasks requiring at least one of motion of the limb around the joint or locking of the limb in a fixed position relative to the joint,
   wherein the wearable action-assisting device includes:
   a control unit;
   an action-assist wearing tool having a first frame and a second frame adapted to be attached to the wearing person, and having the joint at which the first and second frames are coupled;
   a joint angle sensor to detect a rotation angle between the first and second frames around the joint;
   a myoelectricity sensor; and
   a drive source in communication with the myoelectricity sensor, the drive source mounted on the action-assist wearing tool and coupled to the first and second frames to apply a force for driving the first and second frames around the joint, and
   the method further comprises:
   receiving by the control unit the myoelectricity signal from the myoelectricity sensor to output a control signal to a motor of the drive source;
   determining by the control unit whether a difference between a reference parameter signal corresponding to the rotation angle detected by the joint angle sensor and the myoelectricity signal from the myoelectricity sensor is less than a predetermined threshold; and
   decreasing a gain of the motor when the difference is determined as exceeding the predetermined threshold, so as to limit a range of motion of the first and second frames around the joint.

2. The method according to claim 1, wherein the using the wearable action-assisting device includes providing feedback while the wearing person performs a physical task or the series of physical tasks.

3. The method according to claim 1, wherein the using the wearable action-assisting device includes providing an adjustment of a gain from the wearable action-assisting device.

* * * * *